(12) United States Patent
Uragg et al.

(10) Patent No.: US 7,390,812 B2
(45) Date of Patent: *Jun. 24, 2008

(54) N, N'-DISUBSTITUTED PIPERAZINE COMPOUNDS AND THEIR USE AS ANALGESICS

(75) Inventors: Heinz Uragg, Stolberg (DE); Corinne Maul, Aachen (DE); Helmut Buschmann, Esplugues de Llobregat (ES); Bernd Sundermann, Aachen (DE); Hagen-Heinrich Hennies, Simmerath (DE)

(73) Assignee: Gruenenthal GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/866,101

(22) Filed: Jun. 14, 2004

(65) Prior Publication Data

US 2005/0026926 A1  Feb. 3, 2005

Related U.S. Application Data

(63) Continuation of application No. PCT/EP02/13913, filed on Dec. 9, 2002.

(30) Foreign Application Priority Data

Dec. 14, 2001 (DE) ................................ 101 61 644

(51) Int. Cl.
*A61K 31/497* (2006.01)
(52) U.S. Cl. .............................. 514/252.12; 514/252.13; 514/255.03; 544/379; 544/394; 544/401
(58) Field of Classification Search ................. 544/379, 544/394, 401; 514/252.12, 252.13, 255.03
See application file for complete search history.

(56) References Cited

U.S. PATENT DOCUMENTS 4,203,986 A * 5/1980 Joullie et al. ........... 514/252.11
4,518,712 A   5/1985 Fujimura et al.
4,826,844 A * 5/1989 Husbands et al. ...... 514/252.11
6,248,737 B1  6/2001 Buschmann et al.
6,653,508 B2 11/2003 Sattlegger et al.

FOREIGN PATENT DOCUMENTS

DE       26 47 918      10/1976
GB       1525166        10/1976
WO       03/051369    *  6/2003

OTHER PUBLICATIONS

Cazin et al. Chemical Abstracts, vol. 82, No. 132797 (1974).*
Ohtaka et al. Chem. Pharm. Bull. vol. 35, p. 2782-2791 (1987).*
Modern Synthetic reactions by Herbert O. House, p. 184-189 (1965).*
Bradlerova et al. Collect. Czech. Chem. Commun. vol. 55, p. 1854-1865 (1990).*
Light et al. Journal of the American Pharmaceutical Association, vol. XLVI, p. 279-287 (1957).*
Chiang et al. Journal of Ocular Pharmacology and Therapeutics, vol. 14, pp. 313-322 (1998).*
Rall et al., Pathogenesis Of Neurotropic Viral Infections; Fox Chase Cancer Center 2003, Scientific Report.*
Nikolova, "Synthesis and Pharmacological Screening of a Group of Piperazine Derivatives, Analgesic Activity", Il Farmaco, 48(4), 459-472; 1993.
Hashimoto, "Metabolism of a New Analgesic Agent, dl-erythro-1-Phenyl-2-(o-Chlorophenyl) -2-[4-(p-Methoxybenzyl) -1-Piperazinyl]ethanol Dihydrochloride, in Rats", Drug Metabolism and Disposition, pp. 435-441.

* cited by examiner

*Primary Examiner*—James Wilson
*Assistant Examiner*—Ebenezer Sackey
(74) *Attorney, Agent, or Firm*—Crowell & Moring LLP

(57) ABSTRACT

N,N'-disubstituted piperazine compounds, processes for the production thereof, and pharmaceutical preparations containing these compounds. The use of N,N'-disubstituted piperazine compounds for the production of pharmaceutical preparations and in related methods of treatment.

44 Claims, No Drawings

N, N'-DISUBSTITUTED PIPERAZINE COMPOUNDS AND THEIR USE AS ANALGESICS

CROSS-REFERENCE TO RELATED APPLICATIONS

This application is a continuation of International Patent Application No. PCT/EP02/13913, filed Dec. 9, 2002, designating the United States of America, and published in German as WO 03/051855 A1, the entire disclosure of which is incorporated herein by reference. Priority is claimed based on Federal Republic of Germany Patent Application No. DE 101 61 644.9, filed Dec. 14, 2001.

FIELD OF THE INVENTION

The present invention relates to N,N'-disubstituted piperazine compounds, to processes for the production thereof, to pharmaceutical preparations containing these compounds and to the use of N,N'-disubstituted piperazine compounds for the production of pharmaceutical preparations and in related treatment methods.

BACKGROUND OF THE INVENTION

The treatment of pain is of great medical significance. There is a worldwide need for effective pain treatments. The urgency of the requirement for effective therapeutic methods for providing tailored and targeted treatment of chronic and non-chronic pain, this being taken to mean pain treatment which is effective and satisfactory from the patient's standpoint, is evident from the large number of scientific papers relating to applied analgesia and to basic nociception research which have appeared in recent times. The treatment of depression is also of great medical significance.

SUMMARY OF THE INVENTION

One object of the present invention was accordingly to provide novel compounds, which may be used as pharmaceutical active ingredients in pharmaceutical preparations and are particularly suitable for combatting pain, for local anaesthesia, as an antiarrhythmic, antiemetic and/or nootropic (neurotropic), for the treatment and/or therapy of cardiovascular diseases, urinary incontinence, diarrhea, pruritus and/or dependency on alcohol and/or drugs and/or medicines, and/or inflammation, for the treatment of depression, to increase vigilance and/or libido.

According to the invention, this object is achieved by the provision of N,N'-disubstituted piperazine compounds of the general formula I below, since these compounds in particular exhibit an excellent analgesic action and an excellent action against depression.

The invention accordingly provides N,N'-disubstituted piperazine compounds of the general formula I,

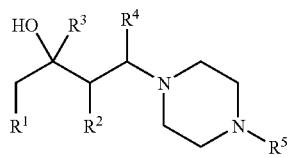

I in which $R^1$ and $R^2$, identical or different, in each case denote a linear or branched, saturated or unsaturated aliphatic residue, or together form a $(CH_2)_n$ chain, wherein n denotes an integer, $R^3$ and $R^5$, identical or different, in each case denote a linear or branched, saturated or unsaturated aliphatic residue, a saturated or unsaturated cycloaliphatic residue, an aryl residue or a heteroaryl residue, wherein the respective ring system may be optionally mono- or polysubstituted and/or attached via a linear or branched, saturated or unsaturated aliphatic bridge and/or the aryl or heteroaryl residue may be part of a polycyclic system, $R^4$ denotes hydrogen or an optionally mono- or polysubstituted aryl or heteroaryl residue with at least one heteroatom, wherein the aryl or heteroaryl residue may be part of a polycyclic system, in the form of the diastereomers thereof, the enantiomers thereof and mixtures thereof—including the racemates thereof—and in the form of corresponding bases, salts and solvates.

Compounds of the general formula I are preferred, in which $R^1$ and $R^2$, identical or different, in each case denote a linear or branched, saturated or unsaturated aliphatic $C_{1-6}$ residue, or together form a $(CH_2)_n$ chain, wherein n denotes an integer from 2-9, $R^3$ denotes a linear or branched, saturated or unsaturated aliphatic $C_{1-6}$ residue, a saturated or unsaturated cycloaliphatic $C_{3-7}$ residue, a phenyl residue or a five- or six-membered heteroaryl residue, wherein the respective ring system may optionally be mono- or polysubstituted and/or attached via a linear or branched, saturated or unsaturated aliphatic $C_{1-5}$ bridge, $R^4$ denotes hydrogen or a phenyl residue, $R^5$ denotes a linear or branched, saturated or unsaturated aliphatic $C_{1-6}$ residue or an optionally substituted phenyl residue.

Compounds of the general formula I are additionally preferred, in which $R^1$ and $R^2$, identical or different, in each case denote a linear or branched, saturated or unsaturated aliphatic $C_{1-3}$ residue, or together form a $(CH_2)_n$ chain, wherein n denotes an integer from 2-9, $R^3$ denotes a linear or branched, saturated or unsaturated aliphatic $C_{1-3}$ residue, a saturated or unsaturated cycloaliphatic $C_{5-6}$ residue, a phenyl residue or a five- or six-membered heteroaryl residue, wherein the respective ring system may optionally be mono- or polysubstituted with halogen, an alkyl group, an alkoxy group and/or a trihalogenated alkyl group and/or may be attached via a linear or branched, saturated or unsaturated aliphatic $C_{13}$ bridge, $R^4$ denotes hydrogen or a phenyl residue, $R^5$ denotes a linear or branched, saturated or unsaturated aliphatic $C_{1-3}$ residue or a phenyl residue optionally substituted with halogen or an alkoxy group.

Compounds of the general formula I are additionally preferred, in which $R^1$ and $R^2$ in each case denote a methyl group, or together form a $(CH_2)_n$ chain, wherein n denotes 3, 4, 5 or 9, $R^3$ denotes a vinyl residue, a cyclopentyl residue, a cyclohexyl residue, a thiophenyl residue or a phenyl residue, wherein the cyclohexyl residue may optionally be attached via a methylene bridge or the phenyl residue may optionally be mono- or polysubstituted with fluorine, chlorine, a methyl group, an isopropyl group, a methoxy group and/or a trifluoroethyl group and/or may optionally be attached via a linear saturated aliphatic $C_{1-3}$ bridge or an ethynyl bridge, $R^4$ denotes hydrogen or a phenyl residue, $R^5$ denotes a methyl group or a phenyl residue optionally substituted with chlorine or a methoxy group.

Particularly preferred compounds are those of the general formula II,

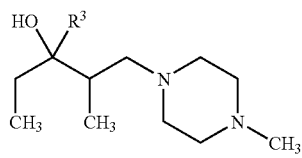

II in which $R^3$ denotes a linear or branched, saturated or unsaturated aliphatic residue, a saturated or unsaturated cycloaliphatic residue, an aryl residue or a heteroaryl residue, wherein the respective ring system may be optionally mono- or polysubstituted and/or attached via a linear or branched, saturated or unsaturated aliphatic bridge and/or the aryl or heteroaryl residue may be part of a polycyclic system.

Particularly preferred compounds are those of the general formula III,

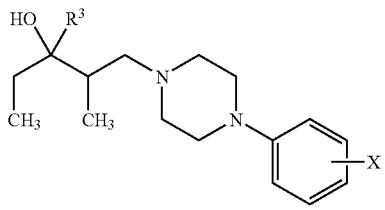

III in which

X denotes hydrogen, halogen or an alkoxy group, preferably hydrogen, chlorine or a methoxy group, and $R^3$ denotes a linear or branched, saturated or unsaturated aliphatic residue, a saturated or unsaturated cycloaliphatic residue, an aryl residue or a heteroaryl residue, wherein the respective ring system may be optionally mono- or polysubstituted and/or attached via a linear or branched, saturated or unsaturated aliphatic bridge and/or the aryl or heteroaryl residue may be part of a polycyclic system.

Particularly preferred compounds are those of the general formula IV,

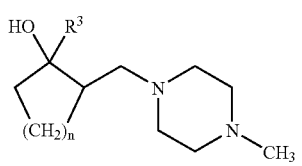

IV in which n denotes an integer from 2-9 and $R^3$ denotes a linear or branched, saturated or unsaturated aliphatic residue, a saturated or unsaturated cycloaliphatic residue, an aryl residue or a heteroaryl residue, wherein the respective ring system may be optionally mono- or polysubstituted and/or attached via a linear or branched, saturated or unsaturated aliphatic bridge and/or the aryl or heteroaryl residue may be part of a polycyclic system.

Particularly preferred compounds are those of the general formula V,

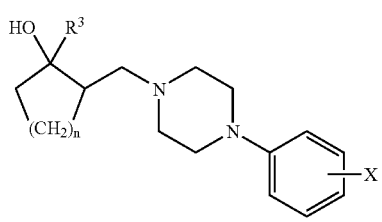

V in which n denotes an integer from 2-9,

X denotes hydrogen, halogen or an alkoxy group, preferably hydrogen, chlorine or a methoxy group, and $R^3$ denotes a linear or branched, saturated or unsaturated aliphatic residue, a saturated or unsaturated cycloaliphatic residue, an aryl residue or a heteroaryl residue, wherein the respective ring system may be optionally mono- or polysubstituted and/or attached via a linear or branched, saturated or unsaturated aliphatic bridge and/or the aryl or heteroaryl residue may be part of a polycyclic system.

Particularly preferred compounds are those of the general formula VI,

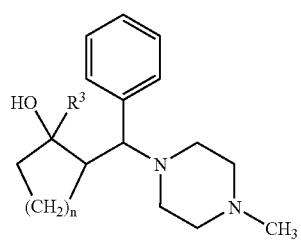

VI in which n denotes an integer from 2-9 and $R^3$ denotes a linear or branched, saturated or unsaturated aliphatic residue, a saturated or unsaturated cycloaliphatic residue, an aryl residue or a heteroaryl residue, wherein the respective ring system may be optionally mono- or polysubstituted and/or attached via a linear or branched, saturated or unsaturated aliphatic bridge and/or the aryl or heteroaryl residue may be part of a polycyclic system.

Particularly preferred compounds are those of the general formula VII,

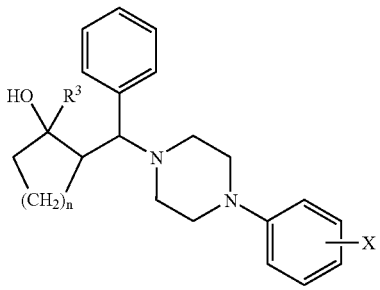
VII in which
n denotes an integer from 2-9,
X denotes hydrogen, halogen or an alkoxy group, preferably hydrogen, chlorine or a methoxy group, and
R³ denotes a linear or branched, saturated or unsaturated aliphatic residue, a saturated or unsaturated cycloaliphatic residue, an aryl residue or a heteroaryl residue, wherein the respective ring system may be optionally mono- or polysubstituted and/or attached via a linear or branched, saturated or unsaturated aliphatic bridge and/or the aryl or heteroaryl residue may be part of a polycyclic system.

Compounds of the general formulae II-VII are additionally preferred, in which
R³ denotes a linear or branched, saturated or unsaturated aliphatic $C_{1-6}$ residue, a saturated or unsaturated cycloaliphatic $C_{3-7}$ residue, a phenyl residue or a five- or six-membered heteroaryl residue, wherein the respective ring system may optionally be mono- or polysubstituted and/or attached via a linear or branched, saturated or unsaturated aliphatic $C_{1-5}$ bridge
and the other symbols have the above-stated meaning.

Compounds of the general formulae II-VII are additionally preferred, in which
R³ denotes a linear or branched, saturated or unsaturated aliphatic $C_{1-3}$ residue, a saturated or unsaturated cycloaliphatic $C_{5-6}$ residue, a phenyl residue or a five- or six-membered heteroaryl residue, wherein the respective ring system may optionally be mono- or polysubstituted with halogen, an alkyl group, an alkoxy group and/or a trihalogenated alkyl group and/or may be attached via a linear or branched, saturated or unsaturated aliphatic $C_{1-3}$ bridge
and the other symbols have the above-stated meaning.

Compounds of the general formulae II-VII are additionally preferred, in which
R³ denotes a vinyl residue, a cyclopentyl residue, a cyclohexyl residue, a thiophenyl residue or a phenyl residue, wherein the cyclohexyl residue may optionally be attached via a methylene bridge or the phenyl residue may optionally be mono- or polysubstituted with fluorine, chlorine, a methyl group, an isopropyl group, a methoxy group and/or a trifluoroethyl group and/or may optionally be attached via a linear saturated aliphatic $C_{1-3}$ bridge or an ethynyl bridge
and the other symbols have the above-stated meaning.

A heteroaryl residue is understood to be an optionally mono- or polysubstituted, five- or six-membered aromatic residue with at least one, optionally 2, 3, 4 or 5 heteroatoms, which may be identical or different, which residue may be part of a polycyclic system. Preferred heteroatoms are nitrogen, oxygen and sulfur. Heteroaryl residues are particularly preferably selected from the group comprising pyrrolyl, indolyl, furyl (furanyl), benzofuranyl, thienyl (thiophenyl), benzothienyl, pyrazolyl, imidazolyl, thiazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl and phenothiazinyl residues. Attachment may be effected via any desired bondable ring atom. The optionally present substituents may be identical or different and attached to any desired, bondable ring atom.

An aryl residue is understood to mean an optionally mono- or polysubstituted aromatic residue, which may be part of a polycyclic system. A phenyl residue is particularly preferred. Attachment may be effected via any desired bondable ring atom. The optionally present substituents may be identical or different and attached to any desired, bondable ring atom.

Very particularly preferred are compounds selected from the group comprising
2-Methyl-1-(4-methyl-piperazin-1-yl)-3-phenyl-pentan-3-ol
3-(4-Chloro-phenyl)-2-methyl-1-(4-methyl-piperazin-1-yl)-pentan-3-ol
3-Benzyl-2-methyl-1-(4-methyl-piperazin-1-yl)-pentan-3-ol
3-(4-Fluoro-3-methyl-phenyl)-2-methyl-1-(4-methyl-piperazin-1-yl)-pentan-3-ol
2-Methyl-1-(4-methyl-piperazin-1-yl)-3-o-tolyl-pentan-3-ol
3-Ethyl-4-methyl-5-(4-methyl-piperazin-1-yl)-pent-1-en-3-ol
3-(4-tert-Butyl-phenyl)-2-methyl-1-(4-methyl-piperazin-1-yl)-pentan-3-ol
3-Cyclopentyl-2-methyl-1-(4-methyl-piperazin-1-yl)-pentan-3-ol
2-Methyl-1-(4-methyl-piperazin-1-yl)-3-m-tolyl-pentan-3-ol
3-Cyclohexyl-2-methyl-1-(4-methyl-piperazin-1-yl)-pentan-3-ol
3-(4-Fluoro-phenyl)-2-methyl-1-(4-methyl-piperazin-1-yl)-pentan-3-ol
3-Ethyl-2-methyl-1-(4-methyl-piperazin-1-yl)-5-phenyl-pentan-3-ol
3-Ethyl-4-methyl-5-(4-methyl-piperazin-1-yl)-1-phenyl-pent-1-yn-3-ol
2-Methyl-1-(4-methyl-piperazin-1-yl)-3-thiophen-2-yl-pentan-3-ol
3-(3-Methoxy-phenyl)-2-methyl-1-(4-methyl-piperazin-1-yl)-pentan-3-ol
3-Ethyl-2-methyl-1-(4-methyl-piperazin-1-yl)-6-phenyl-hexan-3-ol
2-Methyl-1-(4-methyl-piperazin-1-yl)-3-p-tolyl-pentan-3-ol
3-(4-Methoxy-phenyl)-2-methyl-1-(4-methyl-piperazin-1-yl)-pentan-3-ol
2-(4-Methyl-piperazin-1-ylmethyl)-1-phenyl-cyclohexanol
1-Benzyl-2-(4-methyl-piperazin-1-ylmethyl)-cyclohexanol
1-(4-Fluoro-3-methyl-phenyl)-2-(4-methyl-piperazin-1-ylmethyl)-cyclohexanol
2-(4-Methyl-piperazin-1-ylmethyl)-1-o-tolyl-cyclohexanol
2-(4-Methyl-piperazin-1-ylmethyl)-1-vinyl-cyclohexanol
1-Cyclopentyl-2-(4-methyl-piperazin-1-ylmethyl)-cyclohexanol
2-(4-Methyl-piperazin-1-ylmethyl)-1-m-tolyl-cyclohexanol
2-(4-Methyl-piperazin-1-ylmethyl)-bicyclohexyl-1-ol
1-(4-Fluoro-phenyl)-2-(4-methyl-piperazin-1-ylmethyl)-cyclohexanol
2-(4-Methyl-piperazin-1-ylmethyl)-1-phenethyl-cyclohexanol
2-(4-Methyl-piperazin-1-ylmethyl)-1-thiophen-2-yl-cyclohexanol 1-(2,4-Dichloro-phenyl)-2-(4-methyl-piperazin-1-ylmethyl)-cyclohexanol
1-(3-Methoxy-phenyl)-2-(4-methyl-piperazin-1-ylmethyl)-cyclohexanol
2-(4-Methyl-piperazin-1-ylmethyl)-1-(3-phenyl-propyl)-cyclohexanol
2-(4-Methyl-piperazin-1-ylmethyl)-1-p-tolyl-cyclohexanol
1-(4-Methoxy-phenyl)-2-(4-methyl-piperazin-1-ylmethyl)-cyclohexanol
1-Benzyl-2-(4-methyl-piperazin-1-ylmethyl)-cyclooctanol
2-(4-Methyl-piperazin-1-ylmethyl)-1-vinyl-cyclooctanol
1-(4-tert-Butyl-phenyl)-2-(4-methyl-piperazin-1-ylmethyl)-cyclooctanol
1-Cyclopentyl-2-(4-methyl-piperazin-1-ylmethyl)-cyclooctanol
2-(4-Methyl-piperazin-1-ylmethyl)-1-phenethyl-cyclooctanol
2-(4-Methyl-piperazin-1-ylmethyl)-1-phenylethynyl-cyclooctanol
2-(4-Methyl-piperazin-1-ylmethyl)-1-thiophen-2-yl-cyclooctanol
1-(3-Methoxy-phenyl)-2-(4-methyl-piperazin-1-ylmethyl)-cyclooctanol
2-(4-Methyl-piperazin-1-ylmethyl)-1-(3-phenyl-propyl)-cyclooctanol
2-(4-Methyl-piperazin-1-ylmethyl)-1-p-tolyl-cyclooctanol
1-(4-Methoxy-phenyl)-2-(4-methyl-piperazin-1-ylmethyl)-cyclooctanol
2-(4-Methyl-piperazin-1-ylmethyl)-1-phenyl-cycloheptanol
1-(4-Chloro-phenyl)-2-(4-methyl-piperazin-1-ylmethyl)-cycloheptanol
1-Benzyl-2-(4-methyl-piperazin-1-ylmethyl)-cycloheptanol
1-(4-Fluoro-3-methyl-phenyl)-2-(4-methyl-piperazin-1-ylmethyl)-cycloheptanol
2-(4-Methyl-piperazin-1-ylmethyl)-1-o-tolyl-cycloheptanol
2-(4-Methyl-piperazin-1-ylmethyl)-1-vinyl-cycloheptanol
1-(4-tert-Butyl-phenyl)-2-(4-methyl-piperazin-1-ylmethyl)-cycloheptanol
1-Cyclopentyl-2-(4-methyl-piperazin-1-ylmethyl)-cycloheptanol
2-(4-Methyl-piperazin-1-ylmethyl)-1-m-tolyl-cycloheptanol
1-[4-(3-Chloro-phenyl)-piperazin-1-yl]-2-methyl-3-phenyl-pentan-3-ol
3-(4-Chloro-phenyl)-1-[4-(3-chloro-phenyl)-piperazin-1-yl]-2-methyl-pentan-3-ol
3-Benzyl-1-[4-(3-chloro-phenyl)-piperazin-1-yl]-2-methyl-pentan-3-ol
1-[4-(3-Chloro-phenyl)-piperazin-1-yl]-3-(4-fluoro-3-methyl-phenyl)-2-methyl-pentan-3-ol
5-[4-(3-Chloro-phenyl)-piperazin-1-yl]-3-ethyl-4-methyl-pent-1-en-3-ol
3-(4-tert-Butyl-phenyl)-1-[4-(3-chloro-phenyl)-piperazin-1-yl]-2-methyl-pentan-3-ol
1-[4-(3-Chloro-phenyl)-piperazin-1-yl]-2-methyl-3-m-tolyl-pentan-3-ol
1-[4-(3-Chloro-phenyl)-piperazin-1-yl]-3-cyclohexyl-2-methyl-pentan-3-ol
1-[4-(3-Chloro-phenyl)-piperazin-1-yl]-3-(4-fluoro-phenyl)-2-methyl-pentan-3-ol
1-[4-(3-Chloro-phenyl)-piperazin-1-yl]-3-ethyl-2-methyl-5-phenyl-pentan-3-ol
5-[4-(3-Chloro-phenyl)-piperazin-1-yl]-3-ethyl-4-methyl-1-phenyl-pent-1-yn-3-ol
1-[4-(3-Chloro-phenyl)-piperazin-1-yl]-2-methyl-3-thiophen-2-yl-pentan-3-ol
1-[4-(3-Chloro-phenyl)-piperazin-1-yl]-3-(3-methoxy-phenyl)-2-methyl-pentan-3-ol
1-[4-(3-Chloro-phenyl)-piperazin-1-yl]-3-ethyl-2-methyl-6-phenyl-hexan-3-ol
1-[4-(3-Chloro-phenyl)-piperazin-1-yl]-2-methyl-3-p-tolyl-pentan-3-ol
1-[4-(3-Chloro-phenyl)-piperazin-1-yl]-3-(4-methoxy-phenyl)-2-methyl-pentan-3-ol
1-[4-(3-Chloro-phenyl)-piperazin-1-yl]-3-(5-fluoro-2-methoxy-phenyl)-2-methyl-pentan-3-ol
1-[4-(3-Chloro-phenyl)-piperazin-1-yl]-3-(3-fluoro-phenyl)-2-methyl-pentan-3-ol
3-(3-Chloro-phenyl)-1-[4-(3-chloro-phenyl)-piperazin-1-yl]-2-methyl-pentan-3-ol
3-(2-Chloro-benzyl)-1-[4-(3-chloro-phenyl)-piperazin-1-yl]-2-methyl-pentan-3-ol
1-[4-(3-Chloro-phenyl)-piperazin-1-yl]-3-(4-fluoro-benzyl)-2-methyl-pentan-3-ol
1-[4-(3-Chloro-phenyl)-piperazin-1-yl]-3-(3-methoxy-benzyl)-2-methyl-pentan-3-ol
1-[4-(3-Chloro-phenyl)-piperazin-1-yl]-3-(3-fluoro-benzyl)-2-methyl-pentan-3-ol
1-[4-(3-Chloro-phenyl)-piperazin-1-yl]-3-(2-methoxy-phenyl)-2-methyl-pentan-3-ol
1-[4-(3-Chloro-phenyl)-piperazin-1-yl]-2-methyl-3-(2-methyl-benzyl)-pentan-3-ol
1-[4-(3-Chloro-phenyl)-piperazin-1-yl]-2-methyl-3-(3-trifluoromethyl-phenyl)-pentan-3-ol
1-[4-(3-Chloro-phenyl)-piperazin-1-yl]-2-methyl-3-(3-methyl-benzyl)-pentan-3-ol
3-(4-Chloro-benzyl)-1-[4-(3-chloro-phenyl)-piperazin-1-yl]-2-methyl-pentan-3-ol
3-(2-Chloro-6-fluoro-benzyl)-1-[4-(3-chloro-phenyl)-piperazin-1-yl]-2-methyl-pentan-3-ol
1-[4-(3-Chloro-phenyl)-piperazin-1-yl]-3-(2,5-dimethyl-benzyl)-2-methyl-pentan-3-ol
3-(3-Chloro-benzyl)-1-[4-(3-chloro-phenyl)-piperazin-1-yl]-2-methyl-pentan-3-ol
1-[4-(3-Chloro-phenyl)-piperazin-1-yl]-3-(2,4-dichloro-benzyl)-2-methyl-pentan-3-ol
3-Cyclohexylmethyl-2-methyl-1-(4-methyl-piperazin-1-yl)-pentan-3-ol
3-(5-Fluoro-2-methoxy-phenyl)-2-methyl-1-(4-methyl-piperazin-1-yl)-pentan-3-ol
3-(3-Fluoro-phenyl)-2-methyl-1-(4-methyl-piperazin-1-yl)-pentan-3-ol
3-(3-Chloro-phenyl)-2-methyl-1-(4-methyl-piperazin-1-yl)-pentan-3-ol
3-(3,5-Dichloro-phenyl)-2-methyl-1-(4-methyl-piperazin-1-yl)-pentan-3-ol
3-(2-Chloro-benzyl)-2-methyl-1-(4-methyl-piperazin-1-yl)-pentan-3-ol
3-(4-Fluoro-benzyl)-2-methyl-1-(4-methyl-piperazin-1-yl)-pentan-3-ol
3-(3-Methoxy-benzyl)-2-methyl-1-(4-methyl-piperazin-1-yl)-pentan-3-ol
3-(4-Chloro-3-trifluoromethyl-phenyl)-2-methyl-1-(4-methyl-piperazin-1-yl)-pentan-3-ol
3-(3-Fluoro-benzyl)-2-methyl-1-(4-methyl-piperazin-1-yl)-pentan-3-ol
3-(2-Methoxy-phenyl)-2-methyl-1-(4-methyl-piperazin-1-yl)-pentan-3-ol
2-Methyl-3-(2-methyl-benzyl)-1-(4-methyl-piperazin-1-yl)-pentan-3-ol
3-(3-Chloro-4-fluoro-phenyl)-2-methyl-1-(4-methyl-piperazin-1-yl)-pentan-3-ol 2-Methyl-1-(4-methyl-piperazin-1-yl)-3-(3-trifluoromethyl-phenyl)-pentan-3-ol
2-Methyl-3-(3-methyl-benzyl)-1-(4-methyl-piperazin-1-yl)-pentan-3-ol
3-(4-Chloro-benzyl)-2-methyl-1-(4-methyl-piperazin-1-yl)-pentan-3-ol
3-(2-Chloro-6-fluoro-benzyl)-2-methyl-1-(4-methyl-piperazin-1-yl)-pentan-3-ol
3-(2,5-Dimethyl-benzyl)-2-methyl-1-(4-methyl-piperazin-1-yl)-pentan-3-ol
3-(3-Chloro-benzyl)-2-methyl-1-(4-methyl-piperazin-1-yl)-pentan-3-ol
3-(2,4-Dichloro-benzyl)-2-methyl-1-(4-methyl-piperazin-1-yl)-pentan-3-ol
1-Cyclohexylmethyl-2-(4-methyl-piperazin-1-ylmethyl)-cyclohexanol
1-(5-Fluoro-2-methoxy-phenyl)-2-(4-methyl-piperazin-1-ylmethyl)-cyclohexanol
1-(3-Fluoro-phenyl)-2-(4-methyl-piperazin-1-ylmethyl)-cyclohexanol
1-(3-Chloro-phenyl)-2-(4-methyl-piperazin-1-ylmethyl)-cyclohexanol
1-(3,5-Dichloro-phenyl)-2-(4-methyl-piperazin-1-ylmethyl)-cyclohexanol
1-(2-Chloro-benzyl)-2-(4-methyl-piperazin-1-ylmethyl)-cyclohexanol
1-(4-Fluoro-benzyl)-2-(4-methyl-piperazin-1-ylmethyl)-cyclohexanol
1-(3-Methoxy-benzyl)-2-(4-methyl-piperazin-1-ylmethyl)-cyclohexanol
1-(4-Chloro-3-trifluoromethyl-phenyl)-2-(4-methyl-piperazin-1-ylmethyl)-cyclohexanol
1-(3-Fluoro-benzyl)-2-(4-methyl-piperazin-1-ylmethyl)-cyclohexanol
1-(2-Methoxy-phenyl)-2-(4-methyl-piperazin-1-ylmethyl)-cyclohexanol
1-(2-Methyl-benzyl)-2-(4-methyl-piperazin-1-ylmethyl)-cyclohexanol
1-(3-Chloro-4-fluoro-phenyl)-2-(4-methyl-piperazin-1-ylmethyl)-cyclohexanol
2-(4-Methyl-piperazin-1-ylmethyl)-1-(3-trifluoromethyl-phenyl)-cyclohexanol
1-(3-Methyl-benzyl)-2-(4-methyl-piperazin-1-ylmethyl)-cyclohexanol
1-(4-Chloro-benzyl)-2-(4-methyl-piperazin-1-ylmethyl)-cyclohexanol
1-(2,5-Dimethyl-benzyl)-2-(4-methyl-piperazin-1-ylmethyl)-cyclohexanol
1-(3-Chloro-benzyl)-2-(4-methyl-piperazin-1-ylmethyl)-cyclohexanol
1-(2,4-Dichloro-benzyl)-2-(4-methyl-piperazin-1-ylmethyl)-cyclohexanol
1-Cyclohexylmethyl-2-(4-methyl-piperazin-1-ylmethyl)-cyclooctanol
1-(5-Fluoro-2-methoxy-phenyl)-2-(4-methyl-piperazin-1-ylmethyl)-cyclooctanol
1-(2-Chloro-benzyl)-2-(4-methyl-piperazin-1-ylmethyl)-cyclooctanol
1-(4-Fluoro-benzyl)-2-(4-methyl-piperazin-1-ylmethyl)-cyclooctanol
1-(3-Fluoro-benzyl)-2-(4-methyl-piperazin-1-ylmethyl)-cyclooctanol
1-(2-Methoxy-phenyl)-2-(4-methyl-piperazin-1-ylmethyl)-cyclooctanol
1-(3-Methyl-benzyl)-2-(4-methyl-piperazin-1-ylmethyl)-cyclooctanol
1-(4-Chloro-benzyl)-2-(4-methyl-piperazin-1-ylmethyl)-cyclooctanol
1-(2-Chloro-6-fluoro-benzyl)-2-(4-methyl-piperazin-1-ylmethyl)-cyclooctanol
1-(2,5-Dimethyl-benzyl)-2-(4-methyl-piperazin-1-ylmethyl)-cyclooctanol
1-(3-Chloro-benzyl)-2-(4-methyl-piperazin-1-ylmethyl)-cyclooctanol
1-(2,4-Dichloro-benzyl)-2-(4-methyl-piperazin-1-ylmethyl)-cyclooctanol
1-Cyclohexylmethyl-2-(4-methyl-piperazin-1-ylmethyl)-cycloheptanol
1-(5-Fluoro-2-methoxy-phenyl)-2-(4-methyl-piperazin-1-ylmethyl)-cycloheptanol
1-(3-Fluoro-phenyl)-2-(4-methyl-piperazin-1-ylmethyl)-cycloheptanol
1-(3-Chloro-phenyl)-2-(4-methyl-piperazin-1-ylmethyl)-cycloheptanol
1-(3,5-Dichloro-phenyl)-2-(4-methyl-piperazin-1-ylmethyl)-cycloheptanol
1-(2-Chloro-benzyl)-2-(4-methyl-piperazin-1-ylmethyl)-cycloheptanol
1-(4-Fluoro-benzyl)-2-(4-methyl-piperazin-1-ylmethyl)-cycloheptanol
1-(3-Methoxy-benzyl)-2-(4-methyl-piperazin-1-ylmethyl)-cycloheptanol
1-(4-Chloro-3-trifluoromethyl-phenyl)-2-(4-methyl-piperazin-1-ylmethyl)-cycloheptanol
1-(3-Fluoro-benzyl)-2-(4-methyl-piperazin-1-ylmethyl)-cycloheptanol
1-(2-Methoxy-phenyl)-2-(4-methyl-piperazin-1-ylmethyl)-cycloheptanol
1-(2-Methyl-benzyl)-2-(4-methyl-piperazin-1-ylmethyl)-cycloheptanol
1-(3-Chloro-4-fluoro-phenyl)-2-(4-methyl-piperazin-1-ylmethyl)-cycloheptanol
2-(4-Methyl-piperazin-1-ylmethyl)-1-(3-trifluoromethyl-phenyl)-cycloheptanol
1-(3-Methyl-benzyl)-2-(4-methyl-piperazin-1-ylmethyl)-cycloheptanol
1-(4-Chloro-benzyl)-2-(4-methyl-piperazin-1-ylmethyl)-cycloheptanol
1-(2-Chloro-6-fluoro-benzyl)-2-(4-methyl-piperazin-1-ylmethyl)-cycloheptanol
1-(2,5-Dimethyl-benzyl)-2-(4-methyl-piperazin-1-ylmethyl)-cycloheptanol
1-(3-Chloro-benzyl)-2-(4-methyl-piperazin-1-ylmethyl)-cycloheptanol
1-(2,4-Dichloro-benzyl)-2-(4-methyl-piperazin-1-ylmethyl)-cycloheptanol
1-Benzyl-2-(4-methyl-piperazin-1-ylmethyl)-cyclododecanol
2-(4-Methyl-piperazin-1-ylmethyl)-1-vinyl-cyclododecanol
1-Cyclopentyl-2-(4-methyl-piperazin-1-ylmethyl)-cyclododecanol
2-(4-Methyl-piperazin-1-ylmethyl)-1-phenethyl-cyclododecanol
2-(4-Methyl-piperazin-1-ylmethyl)-1-phenylethynyl-cyclododecanol
2-(4-Methyl-piperazin-1-ylmethyl)-1-thiophen-2-yl-cyclododecanol
2-(4-Methyl-piperazin-1-ylmethyl)-1-(3-phenyl-propyl)-cyclododecanol
1-(5-Fluoro-2-methoxy-phenyl)-2-(4-methyl-piperazin-1-ylmethyl)-cyclododecanol
1-(2-Chloro-benzyl)-2-(4-methyl-piperazin-1-ylmethyl)-cyclododecanol 1-(4-Fluoro-benzyl)-2-(4-methyl-piperazin-1-ylmethyl)-cyclododecanol
1-(3-Methoxy-benzyl)-2-(4-methyl-piperazin-1-ylmethyl)-cyclododecanol
1-(3-Fluoro-benzyl)-2-(4-methyl-piperazin-1-ylmethyl)-cyclododecanol
1-(2-Methoxy-phenyl)-2-(4-methyl-piperazin-1-ylmethyl)-cyclododecanol
1-(2-Methyl-benzyl)-2-(4-methyl-piperazin-1-ylmethyl)-cyclododecanol
1-(3-Methyl-benzyl)-2-(4-methyl-piperazin-1-ylmethyl)-cyclododecanol
1-(4-Chloro-benzyl)-2-(4-methyl-piperazin-1-ylmethyl)-cyclododecanol
1-(2,5-Dimethyl-benzyl)-2-(4-methyl-piperazin-1-ylmethyl)-cyclododecanol
1-(3-Chloro-benzyl)-2-(4-methyl-piperazin-1-ylmethyl)-cyclododecanol
1-(2,4-Dichloro-benzyl)-2-(4-methyl-piperazin-1-ylmethyl)-cyclododecanol
2-[4-(3-Chloro-phenyl)-piperazin-1-ylmethyl]-1-cyclohexylmethyl-cyclohexanol
2-[4-(3-Chloro-phenyl)-piperazin-1-ylmethyl]-1-(5-fluoro-2-methoxy-phenyl)-cyclohexanol
2-[4-(3-Chloro-phenyl)-piperazin-1-ylmethyl]-1-(3-fluoro-phenyl)-cyclohexanol
1-(3-Chloro-phenyl)-2-[4-(3-chloro-phenyl)-piperazin-1-ylmethyl]-cyclohexanol
2-[4-(3-Chloro-phenyl)-piperazin-1-ylmethyl]-1-(3,5-dichloro-phenyl)-cyclohexanol
1-(2-Chloro-benzyl)-2-[4-(3-chloro-phenyl)-piperazin-1-ylmethyl]-cyclohexanol
2-[4-(3-Chloro-phenyl)-piperazin-1-ylmethyl]-1-(4-fluoro-benzyl)-cyclohexanol
2-[4-(3-Chloro-phenyl)-piperazin-1-ylmethyl]-1-(4-chloro-3-trifluoromethyl-phenyl)-cyclohexanol
2-[4-(3-Chloro-phenyl)-piperazin-1-ylmethyl]-1-(3-fluoro-benzyl)-cyclohexanol
2-[4-(3-Chloro-phenyl)-piperazin-1-ylmethyl]-1-(2-methoxy-phenyl)-cyclohexanol
1-(3-Chloro-4-fluoro-phenyl)-2-[4-(3-chloro-phenyl)-piperazin-1-ylmethyl]-cyclohexanol
2-[4-(3-Chloro-phenyl)-piperazin-1-ylmethyl]-1-(3-trifluoromethyl-phenyl)-cyclohexanol
2-[4-(3-Chloro-phenyl)-piperazin-1-ylmethyl]-1-(3-methyl-benzyl)-cyclohexanol
1-(4-Chloro-benzyl)-2-[4-(3-chloro-phenyl)-piperazin-1-ylmethyl]-cyclohexanol
1-(2-Chloro-6-fluoro-benzyl)-2-[4-(3-chloro-phenyl)-piperazin-1-ylmethyl]-cyclohexanol
2-[4-(3-Chloro-phenyl)-piperazin-1-ylmethyl]-1-(2,5-dimethyl-benzyl)-cyclohexanol
1-(3-Chloro-benzyl)-2-[4-(3-chloro-phenyl)-piperazin-1-ylmethyl]-cyclohexanol
2-[4-(2-Chloro-phenyl)-piperazin-1-ylmethyl]-1-phenyl-cyclohexanol
1-(4-Chloro-phenyl)-2-[4-(2-chloro-phenyl)-piperazin-1-ylmethyl]-cyclohexanol
1-Benzyl-2-[4-(2-chloro-phenyl)-piperazin-1-ylmethyl]-cyclohexanol
2-[4-(2-Chloro-phenyl)-piperazin-1-ylmethyl]-1-(4-fluoro-3-methyl-phenyl)-cyclohexanol
2-[4-(2-Chloro-phenyl)-piperazin-1-ylmethyl]-1-o-tolyl-cyclohexanol
2-[4-(2-Chloro-phenyl)-piperazin-1-ylmethyl]-1-vinyl-cyclohexanol
1-(4-tert-Butyl-phenyl)-2-[4-(2-chloro-phenyl)-piperazin-1-ylmethyl]-cyclohexanol
2-[4-(2-Chloro-phenyl)-piperazin-1-ylmethyl]-1-cyclopentyl-cyclohexanol
2-[4-(2-Chloro-phenyl)-piperazin-1-ylmethyl]-1-m-tolyl-cyclohexanol
2-[4-(2-Chloro-phenyl)-piperazin-1-ylmethyl]-bicyclohexyl-1-ol
2-[4-(2-Chloro-phenyl)-piperazin-1-ylmethyl]-1-(4-fluoro-phenyl)-cyclohexanol
2-[4-(2-Chloro-phenyl)-piperazin-1-ylmethyl]-1-phenethyl-cyclohexanol
2-[4-(2-Chloro-phenyl)-piperazin-1-ylmethyl]-1-phenylethynyl-cyclohexanol
2-[4-(2-Chloro-phenyl)-piperazin-1-ylmethyl]-1-thiophen-2-yl-cyclohexanol
2-[4-(2-Chloro-phenyl)-piperazin-1-ylmethyl]-1-(3-methoxy-phenyl)-cyclohexanol
2-[4-(2-Chloro-phenyl)-piperazin-1-ylmethyl]-1-(3-phenyl-propyl)-cyclohexanol
2-[4-(2-Chloro-phenyl)-piperazin-1-ylmethyl]-1-p-tolyl-cyclohexanol
2-[4-(2-Chloro-phenyl)-piperazin-1-ylmethyl]-1-(4-methoxy-phenyl)-cyclohexanol
2-[4-(2-Chloro-phenyl)-piperazin-1-ylmethyl]-1-cyclohexylmethyl-cyclohexanol
2-[4-(2-Chloro-phenyl)-piperazin-1-ylmethyl]-1-(5-fluoro-2-methoxy-phenyl)-cyclohexanol
1-(3-Chloro-phenyl)-2-[4-(2-chloro-phenyl)-piperazin-1-ylmethyl]-cyclohexanol
2-[4-(2-Chloro-phenyl)-piperazin-1-ylmethyl]-1-(3,5-dichloro-phenyl)-cyclohexanol
1-(2-Chloro-benzyl)-2-[4-(2-chloro-phenyl)-piperazin-1-ylmethyl]-cyclohexanol
2-[4-(2-Chloro-phenyl)-piperazin-1-ylmethyl]-1-(4-fluoro-benzyl)-cyclohexanol
2-[4-(2-Chloro-phenyl)-piperazin-1-ylmethyl]-1-(3-methoxy-benzyl)-cyclohexanol
2-[4-(2-Chloro-phenyl)-piperazin-1-ylmethyl]-1-(4-chloro-3-trifluoromethyl-phenyl)-cyclohexanol
2-[4-(2-Chloro-phenyl)-piperazin-1-ylmethyl]-1-(3-fluoro-benzyl)-cyclohexanol
2-[4-(2-Chloro-phenyl)-piperazin-1-ylmethyl]-1-(2-methoxy-phenyl)-cyclohexanol
2-[4-(2-Chloro-phenyl)-piperazin-1-ylmethyl]-1-(2-methyl-benzyl)-cyclohexanol
1-(3-Chloro-4-fluoro-phenyl)-2-[4-(2-chloro-phenyl)-piperazin-1-ylmethyl]-cyclohexanol
2-[4-(2-Chloro-phenyl)-piperazin-1-ylmethyl]-1-(3-trifluoromethyl-phenyl)-cyclohexanol
2-[4-(2-Chloro-phenyl)-piperazin-1-ylmethyl]-1-(3-methyl-benzyl)-cyclohexanol
1-(4-Chloro-benzyl)-2-[4-(2-chloro-phenyl)-piperazin-1-ylmethyl]-cyclohexanol
1-(2-Chloro-6-fluoro-benzyl)-2-[4-(2-chloro-phenyl)-piperazin-1-ylmethyl]-cyclohexanol
2-[4-(2-Chloro-phenyl)-piperazin-1-ylmethyl]-1-(2,5-dimethyl-benzyl)-cyclohexanol
1-(3-Chloro-benzyl)-2-[4-(2-chloro-phenyl)-piperazin-1-ylmethyl]-cyclohexanol
2-[4-(2-Chloro-phenyl)-piperazin-1-ylmethyl]-1-(2,4-dichloro-benzyl)-cyclohexanol
2-[4-(2-Methoxy-phenyl)-piperazin-1-ylmethyl]-1-phenyl-cyclohexanol
1-(4-Chloro-phenyl)-2-[4-(2-methoxy-phenyl)-piperazin-1-ylmethyl]-cyclohexanol 1-Benzyl-2-[4-(2-methoxy-phenyl)-piperazin-1-ylmethyl]-cyclohexanol
1-(4-Fluoro-3-methyl-phenyl)-2-[4-(2-methoxy-phenyl)-piperazin-1-ylmethyl]-cyclohexanol
2-[4-(2-Methoxy-phenyl)-piperazin-1-ylmethyl]-1-o-tolyl-cyclohexanol
2-[4-(2-Methoxy-phenyl)-piperazin-1-ylmethyl]-1-vinyl-cyclohexanol
1-(4-tert-Butyl-phenyl)-2-[4-(2-methoxy-phenyl)-piperazin-1-ylmethyl]-cyclohexanol
1-Cyclopentyl-2-[4-(2-methoxy-phenyl)-piperazin-1-ylmethyl]-cyclohexanol
2-[4-(2-Methoxy-phenyl)-piperazin-1-ylmethyl]-1-m-tolyl-cyclohexanol
2-[4-(2-Methoxy-phenyl)-piperazin-1-ylmethyl]-bicyclohexyl-1-ol
1-(4-Fluoro-phenyl)-2-[4-(2-methoxy-phenyl)-piperazin-1-ylmethyl]-cyclohexanol
2-[4-(2-Methoxy-phenyl)-piperazin-1-ylmethyl]-1-phenethyl-cyclohexanol
2-[4-(2-Methoxy-phenyl)-piperazin-1-ylmethyl]-1-phenylethynyl-cyclohexanol
2-[4-(2-Methoxy-phenyl)-piperazin-1-ylmethyl]-1-thiophen-2-yl-cyclohexanol
1-(3-Methoxy-phenyl)-2-[4-(2-methoxy-phenyl)-piperazin-1-ylmethyl]-cyclohexanol
2-[4-(2-Methoxy-phenyl)-piperazin-1-ylmethyl]-1-(3-phenyl-propyl)-cyclohexanol
1-(2,3-Dichloro-phenyl)-2-[4-(2-methoxy-phenyl)-piperazin-1-ylmethyl]-cyclohexanol
2-[4-(2-Methoxy-phenyl)-piperazin-1-ylmethyl]-1-p-tolyl-cyclohexanol
1-(4-Methoxy-phenyl)-2-[4-(2-methoxy-phenyl)-piperazin-1-ylmethyl]-cyclohexanol
1-Cyclohexylmethyl-2-[4-(2-methoxy-phenyl)-piperazin-1-ylmethyl]-cyclohexanol
1-(5-Fluoro-2-methoxy-phenyl)-2-[4-(2-methoxy-phenyl)-piperazin-1-ylmethyl]-cyclohexanol
1-(3-Fluoro-phenyl)-2-[4-(2-methoxy-phenyl)-piperazin-1-ylmethyl]-cyclohexanol
1-(3-Chloro-phenyl)-2-[4-(2-methoxy-phenyl)-piperazin-1-ylmethyl]-cyclohexanol
1-(3,5-Dichloro-phenyl)-2-[4-(2-methoxy-phenyl)-piperazin-1-ylmethyl]-cyclohexanol
1-(2-Chloro-benzyl)-2-[4-(2-methoxy-phenyl)-piperazin-1-ylmethyl]-cyclohexanol
1-(4-Fluoro-benzyl)-2-[4-(2-methoxy-phenyl)-piperazin-1-ylmethyl]-cyclohexanol
1-(3-Methoxy-benzyl)-2-[4-(2-methoxy-phenyl)-piperazin-1-ylmethyl]-cyclohexanol
1-(4-Chloro-3-trifluoromethyl-phenyl)-2-[4-(2-methoxy-phenyl)-piperazin-1-ylmethyl]-cyclohexanol
1-(3-Fluoro-benzyl)-2-[4-(2-methoxy-phenyl)-piperazin-1-ylmethyl]-cyclohexanol
1-(2-Methoxy-phenyl)-2-[4-(2-methoxy-phenyl)-piperazin-1-ylmethyl]-cyclohexanol
2-[4-(2-Methoxy-phenyl)-piperazin-1-ylmethyl]-1-(2-methyl-benzyl)-cyclohexanol
1-(3-Chloro-4-fluoro-phenyl)-2-[4-(2-methoxy-phenyl)-piperazin-1-ylmethyl]-cyclohexanol
2-[4-(2-Methoxy-phenyl)-piperazin-1-ylmethyl]-1-(3-trifluoromethyl-phenyl)-cyclohexanol
2-[4-(2-Methoxy-phenyl)-piperazin-1-ylmethyl]-1-(3-methyl-benzyl)-cyclohexanol
1-(4-Chloro-benzyl)-2-[4-(2-methoxy-phenyl)-piperazin-1-ylmethyl]-cyclohexanol
1-(2-Chloro-6-fluoro-benzyl)-2-[4-(2-methoxy-phenyl)-piperazin-1-ylmethyl]-cyclohexanol
1-(2,5-Dimethyl-benzyl)-2-[4-(2-methoxy-phenyl)-piperazin-1-ylmethyl]-cyclohexanol
1-(3-Chloro-benzyl)-2-[4-(2-methoxy-phenyl)-piperazin-1-ylmethyl]-cyclohexanol
1-(2,4-Dichloro-benzyl)-2-[4-(2-methoxy-phenyl)-piperazin-1-ylmethyl]-cyclohexanol
1-Benzyl-2-[4-(2-methoxy-phenyl)-piperazin-1-ylmethyl]-cyclododecanol
2-[4-(2-Methoxy-phenyl)-piperazin-1-ylmethyl]-1-vinyl-cyclododecanol
1-Phenethyl-2-[phenyl-(4-phenyl-piperazin-1-yl)-methyl]-cyclohexanol
1-Benzyl-2-[(4-methyl-piperazin-1-yl)-phenyl-methyl]-cyclohexanol
1-Benzyl-2-[phenyl-(4-phenyl-piperazin-1-yl)-methyl]-cyclohexanol
2-[(4-Methyl-piperazin-1-yl)-phenyl-methyl]-1-phenethyl-cyclohexanol
2-[4-(2-Methoxy-phenyl)-piperazin-1-ylmethyl]-1-phenethyl-cyclododecanol in the form of the diastereomers thereof, the enantiomers thereof and mixtures thereof—including the racemates—and in the form of the corresponding bases, the corresponding salts and the corresponding solvates.

The invention also provides a process for the production of N,N'-disubstituted piperazine compounds of the general formula I, characterized in that A$_1$) a ketone of the formula (1), in which R$^1$ and R$^2$ have the above-stated meaning,

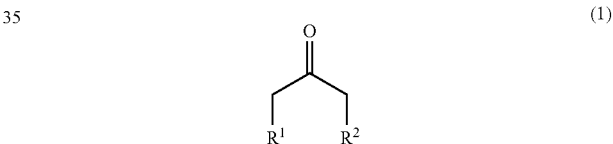

is reacted with paraformaldehyde and a piperazine of the formula (2), in which R$^5$ has the above-stated meaning,

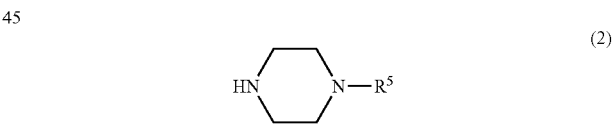

according to a Mannich reaction in a suitable solvent, preferably in ethanol with the addition of hydrochloric acid or in acetic acid, with heating, then the reaction mixture is worked up and the product of the formula (3) is isolated and optionally purified or

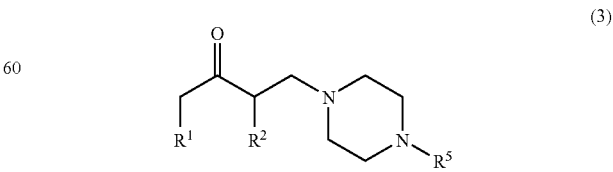

A$_2$) an enamine of the formula (1a), in which R$^1$ and R$^2$ have the above-stated meaning and R denotes an aliphatic C$_{1-6}$ residue, a morpholinyl, piperidyl or pyrrolidinyl residue, wherein the two residues R may be identical or different,

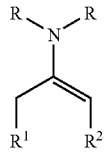

(1a)

is reacted with an aldehyde of the formula (4), in which $R^4$ has the above-stated meaning with the exception of hydrogen,

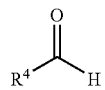

(4)

and a piperazine of the formula (2), in which $R^5$ has the above-stated meaning, optionally in the form of the hydrochloride thereof

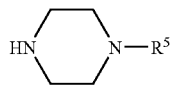

(2)

according to a Mannich reaction in the presence of triethylamine, chlorotrimethylsilane and sodium iodide in a suitable solvent, preferably in acetonitrile, then the reaction mixture is worked up and the product of the formula (3a) is isolated and optionally purified or

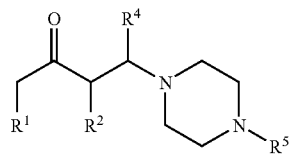

(3a)

$A_3$) an enamine of the formula (1a), in which $R^1$ and $R^2$ have the above-stated meaning and R denotes an aliphatic $C_{1-6}$ residue, a morpholinyl, piperidyl or pyrrolidinyl residue, wherein the two residues R may be identical or different,

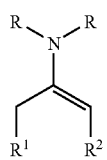

(1a)

is reacted with an iminium salt of the formula (5), in which $R^4$ has the above-stated meaning with the exception of hydrogen and $R^5$ has the above-stated meaning and $Y^-$ denotes a chloride, bromide, iodide or $AlCl_4^-$ ion,

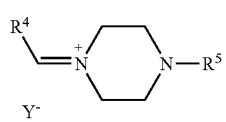

(5)

according to a Mannich reaction in a suitable solvent, preferably in acetonitrile, then the reaction mixture is worked up and the product of the formula (3a) is isolated and optionally purified and

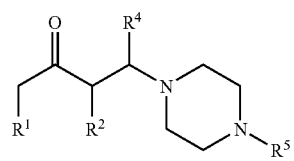

(3a)

B) a compound of the formula (3) or (3a) is reacted with a Grignard compound or an organolithium compound of the formulae $R^3MgCl$, $R^3MgBr$, $R^3MgI$, $MgR^3_2$ or $LiR^3$, in which $R^3$ has the above-stated meaning, in a suitable solvent, preferably diethyl ether or tetrahydrofuran, then the reaction mixture is worked up and the compound of the general formula I is isolated and optionally purified.

The starting compounds used are commercially obtainable or may be obtained using conventional methods known to the person skilled in the art.

The solvents and reaction conditions used for the respective process step correspond to the solvents and reaction conditions conventional for these types of reactions and the reactions are known to the person skilled in the art from the literature.

The free bases of the respective compounds according to the invention of the general formula I may be converted into the corresponding physiologically acceptable salts by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid. The salts formed comprise, inter alia, hydrochlorides, hydrobromides, phosphates, carbonates, hydrogencarbonates, formates, acetates, oxalates, succinates, tartrates, fumarates, citrates and glutamates.

The free bases of the respective compounds according to the invention of the general formula I may be converted into the corresponding hydrochlorides by combining the compounds according to the invention of the general formula I as free bases dissolved in a suitable organic solvent, for example butan-2-one (methyl ethyl ketone), with trimethylsilyl chloride (TMSCl). They may also be converted into the hydrobromides in a corresponding manner.

The hydrates may be formed by crystallization from an aqueous solution.

If the compounds according to the invention of the general formula I are obtained by the production process according to the invention in the form of the racemates thereof or other mixtures of their various enantiomers and/or diastereomers, these may be separated and optionally isolated by conventional processes known to the person skilled in the art. Examples are chromatographic separation processes, in particular liquid chromatography processes at standard pressure or at elevated pressure, preferably MPLC and HPLC processes, and fractional crystallization processes. Individual enantiomers, e.g. diastereomeric salts formed by means of HPLC on a chiral phase or by means of crystallization with chiral acids, such as (+)-tartaric acid, (−)-tartaric acid or (+)-10-camphorsulfonic acid, may here in particular be separated from one another.

The compounds of the general formula I according to the invention are toxicologically safe and are therefore suitable as pharmaceutically active ingredients in pharmaceutical preparations.

The present invention accordingly also provides pharmaceutical preparations, which contain a compound according to the invention of the general formula I, preferably of the general formula II, III, IV, V, VI or VII, as active ingredient and optionally physiologically acceptable auxiliary substances.

If the compounds according to the invention of the general formula I or the corresponding physiologically acceptable salts thereof are chiral, they may be present in the pharmaceutical preparation according to the invention in the form of the enantiomers thereof, the diastereomers thereof or in the form of a mixture of at least two of the above-stated stereoisomers, including the racemates thereof.

The pharmaceutical preparations according to the invention are preferably suitable for the treatment of pain, for local anaesthesia, as an antiarrhythmic, an antiemetic and/or a nootropic (neurotropic), for the treatment of cardiovascular diseases, urinary incontinence, diarrhea, pruritus and/or dependency on alcohol and/or drugs and/or medicines, and/or inflammation, for the treatment of depression, to increase vigilance and/or libido.

The present invention further provides the use of at least one compound of the general formula I, preferably of the general formula II, III, IV, V, VI or VII, for the production of a pharmaceutical preparation for combatting pain, for local anaesthesia, for the treatment of arrhythmias, emesis, cardiovascular diseases, urinary incontinence, diarrhea, pruritus and/or dependency on alcohol and/or drugs and/or medicines, and/or inflammation, for the treatment of depression, to increase drive, vigilance and/or libido.

The pharmaceutical preparations according to the invention may be formulated as liquid, semisolid or solid dosage forms, for example in the form of solutions for injection, drops, succi, syrups, sprays, suspensions, tablets, patches, capsules, dressings, suppositories, ointments, creams, lotions, gels, emulsions, aerosols or in multiparticulate form, for example in the form of pellets or granules, and also be administered as such.

In addition to at least one compound according to the invention of the general formula I, preferably of the general formula II, III, IV, V, VI or VII, the pharmaceutical preparations according to the invention conventionally contain further physiologically acceptable pharmaceutical auxiliary substances, which are preferably selected from the group consisting of matrix materials, fillers, solvents, diluents, surface-active substances, dyes, preservatives, suspending agents, slip agents, lubricants, aromas and binders.

Selection of the physiologically acceptable auxiliary substances and the quantities thereof which are to be used depends upon whether the pharmaceutical preparation is to be administered orally, subcutaneously, parenterally, intravenously, intraperitoneally, intradermally, intramuscularly, intranasally, buccally, rectally or topically, for example onto infections of the skin, mucous membranes and eyes. Preparations in the form of tablets, coated tablets, capsules, granules, pellets, drops, succi and syrups are preferred for oral administration, while solutions, suspensions, readily reconstitutible dried preparations and sprays are preferred for parenteral, topical and inhalatory administration. Compounds according to the invention of the general formula I, preferably of the general formula II, III, IV, V, VI or VII in a depot in dissolved form or in a dressing, optionally with the addition of skin penetration promoters, are suitable percutaneous administration preparations.

Production of the pharmaceutical preparations according to the invention proceeds with the assistance of conventional means, devices, methods and processes known to the person skilled in the art, such as are described for example in "Remington's Pharmaceutical Sciences", ed. A. R. Gennaro, 17th ed., Mack Publishing Company, Easton, Pa. (1985), in particular in part 8, chapters 76 to 93. The corresponding literature description is incorporated herein by reference and is deemed to be part of the disclosure.

The quantity of the respective compound according to the invention of the general formula I, preferably of the general formula II, III, IV, V, VI or VII, to be administered to the patient may vary and is for example dependent on the weight or age of the patient and on the mode of administration, the indication and the severity of the complaint. Conventionally, at least one compound according to the invention of the general formula I, preferably of the general formula II, III, IV, V, VI or VII, is administered in a quantity of 0.005 to 500 mg/kg, preferably of 0.05 to 5 mg/kg, of patient body weight.

EXAMPLES

The following Examples illustrate the preparation of the compounds according to the invention and the efficacy testing performed using the compounds according to the invention.

The chemicals and solvents used were purchased from conventional suppliers (Acros, Avocado, Aldrich, Fluka, Lancaster, Maybridge, Merck, Sigma, TCI etc.) or were synthesized.

Preparation

Mannich Reaction I

One equivalent of the piperazine hydrochloride, 1-1.5 equivalents of the ketone and 1-1.2 equivalents of paraformaldehyde in 8-10 equivalents of acetic acid were heated with stirring for 15-20 minutes to 95-98° C. Then the acetic acid was removed by vacuum distillation under mild conditions and the reaction mixture combined with acetone or successively with acetone and diisopropyl ether. The Mannich compound precipitated out in crystalline form as the hydrochloride.

In some cases, the Mannich reaction could advantageously be performed in ethanol, combined with a few drops of concentrated hydrochloric acid, with refluxing for several hours (5 to 7 hours).

Further purification of the Mannich compound was effected, where necessary, by silica gel chromatography with ethyl acetate as eluent.

Mannich Reaction II

The piperazine compound (1 equivalent) was added to a sodium iodide solution in acetonitrile (2.2 equivalents) with ice cooling. Triethylamine (1 equivalent) and chlorotrimethylsilane (2.2 equivalents) were added dropwise. The suspension was stirred at room temperature for one hour. The aldehyde (1 equivalent) was added with ice cooling and stirring was performed for one hour at room temperature.

The batch was combined with dilute hydrochloric acid with ice cooling and stirred for 15 minutes. The solution was washed 3× with ether. A basic pH value was established with dilute ammonia solution and extraction was performed with ether. After drying over magnesium sulfate, evaporation was performed.

Grignard Reaction

The Mannich compound dissolved in THF (400 μl, 0.5 M) was initially introduced into a heat-treated reaction vessel cooled to −10° C. under inert gas. 2 equivalents of the prepared Grignard or organolithium reagent in THF or diethyl ether (800 μl, 0.5 M) were then added with stirring. The reaction mixture was stirred at room temperature. After three hours it was recooled to −10° C. and hydrolyzed with ammonium chloride solution.

The reaction mixture was extracted twice with ethyl acetate and vacuum-evaporated at 40° C.

To characterize the product, an ESI-MS spectrograph was recorded.

Biochemical Investigations

It was discovered that the compounds according to the invention display a distinct affinity to binding site 2 of the sodium channel (BTX binding) and inhibit synaptosomal noradrenaline reuptake (NA uptake inhibition). In this way, these compounds of the general formula I, preferably of the general formula II, III, IV, V, VI or VII, are also suitable for the treatment of pain, for local anaesthesia, as an antiarrhythmic, an antiemetic and/or a nootropic (neurotropic), for the treatment of cardiovascular diseases, urinary incontinence, diarrhea, pruritus and/or dependency on alcohol and/or drugs and/or medicines, and/or inflammation, for the treatment of depression, to increase vigilance and/or libido.

Investigations Relating to Noradrenaline Reuptake Inhibition (NA Uptake Inhibition)

In order to be able to carry out these in vitro studies, synaptosomes were freshly isolated from rat brain regions. A so-called "$P_2$" fraction was used, which was prepared according to the instructions given by Gray and Whittaker (E. G. Gray and V. P. Whittaker (1962) J. Anat. 76, 79-88). For NA uptake, these vesicular particles were isolated from the hypothalamus of male rat brains.

A detailed description of the method may be found in the literature (M. Ch. Frink, H.-H. Hennies, W. Englberger, M. Haurand and B. Wilffert (1996) Arzneim.-Forsch./Drug Res. 46 (III), 11, 1029-1036).

The following characteristics were determined for the NA transporter:

NA uptake: Km=0.32±0.11 μM

Binding Investigations at Sodium Channel Binding Site 2 (BTX Binding)

Binding site 2 of the sodium channel is the so-called batrachotoxin (BTX) binding site. [$^3$H]-Batrachotoxinin A20 α-benzoate (10 nM in the batch) was used as ligand. These ion channel particles (synaptosomes) were enriched from rat cerebrocortex after Gray and Whittaker (E. G. Gray and V. P. Whittaker (1962) J. Anat. 76, 79-88). The radioactivity measured in the presence of veratridine (0.3 mM in the batch) is defined as non-specific binding.

The assay conditions were as published by Pauwels, Leysen and Laduron (P. J. Pauwels, J. E. Leysen and P. M. Laduron (1986) Eur. J. Pharmacol. 124, 291-298). Incubation at 37° C. for 120 min.

The $K_D$ value for this binding site is 24.63+1.56 nM.

The results of the biochemical investigations are summarized in the following tables.

| NA Uptake | NA uptake inhibition at 10 μM [%] inhibition |
|---|---|
| 3-Ethyl-2-methyl-1-(4-methyl-piperazin-1-yl)-5-phenyl-pentan-3-ol | 88 |
| 1-(4-Fluoro-3-methyl-phenyl)-2-(4-methyl-piperazin-1-ylmethyl)-cyclohexanol | 65 |
| 2-(4-Methyl-piperazin-1-ylmethyl)-1-m-tolyl-cyclohexanol | 44 |
| 1-(4-Fluoro-phenyl)-2-(4-methyl-piperazin-1-ylmethyl)-cyclohexanol | 51 |
| 2-(4-Methyl-piperazin-1-ylmethyl)-1-phenethyl-cyclohexanol | 71 |
| 2-(4-Methyl-piperazin-1-ylmethyl)-1-p-tolyl-cyclohexanol | 75 |
| 2-(4-Methyl-piperazin-1-ylmethyl)-1-phenethyl-cyclooctanol | 61 |
| 2-(4-Methyl-piperazin-1-ylmethyl)-1-phenyl-cycloheptanol | 50 |
| 1-(4-Chloro-phenyl)-2-(4-methyl-piperazin-1-ylmethyl)-cycloheptanol | 70 |
| 1-(4-Fluoro-3-methyl-phenyl)-2-(4-methyl-piperazin-1-ylmethyl)-cycloheptanol | 66 |
| 1-[4-(3-Chloro-phenyl)-piperazin-1-yl]-2-methyl-3-phenyl-pentan-3-ol | 61 |
| 3-(4-Chloro-phenyl)-1-[4-(3-chloro-phenyl)-piperazin-1-yl]-2-methyl-pentan-3-ol | 54 |
| 3-Benzyl-1-[4-(3-chloro-phenyl)-piperazin-1-yl]-2-methyl-pentan-3-ol | 55 |
| 1-[4-(3-Chloro-phenyl)-piperazin-1-yl]-3-(4-fluoro-3-methyl-phenyl)-2-methyl-pentan-3-ol | 39 |
| 5-[4-(3-Chloro-phenyl)-piperazin-1-yl]-3-ethyl-4-methyl-pent-1-en-3-ol | 53 |
| 3-(4-tert-Butyl-phenyl)-1-[4-(3-chloro-phenyl)-piperazin-1-yl]-2-methyl-pentan-3-ol | 62 |
| 1-[4-(3-Chloro-phenyl)-piperazin-1-yl]-2-methyl-3-m-tolyl-pentan-3-ol | 42 |
| 1-[4-(3-Chloro-phenyl)-piperazin-1-yl]-3-cyclohexyl-2-methyl-pentan-3-ol | 73 |
| 1-[4-(3-Chloro-phenyl)-piperazin-1-yl]-3-(4-fluoro-phenyl)-2-methyl-pentan-3-ol | 53 |
| 1-[4-(3-Chloro-phenyl)-piperazin-1-yl]-3-ethyl-2-methyl-5-phenyl-pentan-3-ol | 52 |
| 5-[4-(3-Chloro-phenyl)-piperazin-1-yl]-3-ethyl-4-methyl-1-phenyl-pent-1-yn-3-ol | 46 |
| 1-[4-(3-Chloro-phenyl)-piperazin-1-yl]-2-methyl-3-thiophen-2-yl-pentan-3-ol | 45 |
| 1-[4-(3-Chloro-phenyl)-piperazin-1-yl]-3-ethyl-2-methyl-6-phenyl-hexan-3-ol | 55 |
| 1-[4-(3-Chloro-phenyl)-piperazin-1-yl]-2-methyl-3-p-tolyl-pentan-3-ol | 41 |
| 1-[4-(3-Chloro-phenyl)-piperazin-1-yl]-3-(4-methoxy-phenyl)-2-methyl-pentan-3-ol | 45 |
| 1-[4-(3-Chloro-phenyl)-piperazin-1-yl]-3-(3-fluoro-phenyl)-2-methyl-pentan-3-ol | 53 |
| 3-(3-Chloro-phenyl)-1-[4-(3-chloro-phenyl)-piperazin-1-yl]-2-methyl-pentan-3-ol | 53 |
| 1-[4-(3-Chloro-phenyl)-piperazin-1-yl]-3-(3-fluoro-benzyl)-2-methyl-pentan-3-ol | 50 |
| 1-[4-(3-Chloro-phenyl)-piperazin-1-yl]-2-methyl-3-(3-trifluoromethyl-phenyl)-pentan-3-ol | 65 |
| 1-[4-(3-Chloro-phenyl)-piperazin-1-yl]-2-methyl-3-(3-methyl-benzyl)-pentan-3-ol | 55 |
| 3-(4-Chloro-benzyl)-1-[4-(3-chloro-phenyl)-piperazin-1-yl]-2-methyl-pentan-3-ol | 39 |

| BTX Binding | |
|---|---|
| | BTX binding at 10 μM [%] inhibition |
| 2-Methyl-1-(4-methyl-piperazin-1-yl)-3-phenyl-pentan-3-ol | 58 |
| 3-(4-Chloro-phenyl)-2-methyl-1-(4-methyl-piperazin-1-yl)-pentan-3-ol | 59 |
| 3-Benzyl-2-methyl-1-(4-methyl-piperazin-1-yl)-pentan-3-ol | 42 |
| 3-(4-Fluoro-3-methyl-phenyl)-2-methyl-1-(4-methyl-piperazin-1-yl)-pentan-3-ol | 56 |
| 2-Methyl-1-(4-methyl-piperazin-1-yl)-3-o-tolyl-pentan-3-ol | 43 |
| 3-Ethyl-4-methyl-5-(4-methyl-piperazin-1-yl)-pent-1-en-3-ol | 67 |
| 3-(4-tert-Butyl-phenyl)-2-methyl-1-(4-methyl-piperazin-1-yl)-pentan-3-ol | 68 |
| 3-Cyclohexyl-2-methyl-1-(4-methyl-piperazin-1-yl)-pentan-3-ol | 59 |
| 3-Ethyl-2-methyl-1-(4-methyl-piperazin-1-yl)-5-phenyl-pentan-3-ol | 74 |
| 2-Methyl-1-(4-methyl-piperazin-1-yl)-3-thiophen-2-yl-pentan-3-ol | 47 |
| 3-Ethyl-2-methyl-1-(4-methyl-piperazin-1-yl)-6-phenyl-hexan-3-ol | 74 |
| 2-Methyl-1-(4-methyl-piperazin-1-yl)-3-p-tolyl-pentan-3-ol | 48 |
| 1-Benzyl-2-(4-methyl-piperazin-1-ylmethyl)-cyclohexanol | 71 |
| 1-(4-Fluoro-3-methyl-phenyl)-2-(4-methyl-piperazin-1-ylmethyl)-cyclohexanol | 60 |
| 2-(4-Methyl-piperazin-1-ylmethyl)-1-o-tolyl-cyclohexanol | 50 |
| 1-Cyclopentyl-2-(4-methyl-piperazin-1-ylmethyl)-cyclohexanol | 49 |
| 2-(4-Methyl-piperazin-1-ylmethyl)-1-m-tolyl-cyclohexanol | 58 |
| 2-(4-Methyl-piperazin-1-ylmethyl)-bicyclohexyl-1-ol | 63 |
| 2-(4-Methyl-piperazin-1-ylmethyl)-1-phenethyl-cyclohexanol | 65 |
| 1-(2,4-Dichloro-phenyl)-2-(4-methyl-piperazin-1-ylmethyl)-cyclohexanol | 55 |
| 2-(4-Methyl-piperazin-1-ylmethyl)-1-(3-phenyl-propyl)-cyclohexanol | 80 |
| 2-(4-Methyl-piperazin-1-ylmethyl)-1-p-tolyl-cyclohexanol | 53 |
| 1-Benzyl-2-(4-methyl-piperazin-1-ylmethyl)-cyclooctanol | 75 |
| 1-(4-tert-Butyl-phenyl)-2-(4-methyl-piperazin-1-ylmethyl)-cyclooctanol | 64 |
| 1-Cyclopentyl-2-(4-methyl-piperazin-1-ylmethyl)-cyclooctanol | 48 |
| 2-(4-Methyl-piperazin-1-ylmethyl)-1-phenethyl-cyclooctanol | 78 |
| 2-(4-Methyl-piperazin-1-ylmethyl)-1-thiophen-2-yl-cyclooctanol | 64 |
| 2-(4-Methyl-piperazin-1-ylmethyl)-1-(3-phenyl-propyl)-cyclooctanol | 87 |
| 1-(4-Methoxy-phenyl)-2-(4-methyl-piperazin-1-ylmethyl)-cyclooctanol | 42 |
| 2-(4-Methyl-piperazin-1-ylmethyl)-1-phenyl-cycloheptanol | 63 |
| 1-(4-Chloro-phenyl)-2-(4-methyl-piperazin-1-ylmethyl)-cycloheptanol | 69 |
| 1-Benzyl-2-(4-methyl-piperazin-1-ylmethyl)-cycloheptanol | 86 |
| 1-(4-Fluoro-3-methyl-phenyl)-2-(4-methyl-piperazin-1-ylmethyl)-cycloheptanol | 69 |
| 1-(4-tert-Butyl-phenyl)-2-(4-methyl-piperazin-1-ylmethyl)-cycloheptanol | 80 |
| 1-Cyclopentyl-2-(4-methyl-piperazin-1-ylmethyl)-cycloheptanol | 55 |
| 2-(4-Methyl-piperazin-1-ylmethyl)-1-m-tolyl-cycloheptanol | 44 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. An N,N'-disubstituted piperazine compound corresponding to formula I,

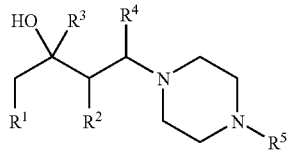

wherein
$R^1$ and $R^2$ together form a $(CH_2)_n$ chain, wherein n denotes an integer from 2 to 9;
$R^3$ denotes a linear or branched, saturated or unsaturated aliphatic $C_{1-6}$ group, a saturated or unsaturated cycloaliphatic $C_{3-7}$ group, a phenyl group, or a thienyl group, wherein the respective ring system of $R^3$ may be unsubstituted or monosubstituted with halogen or mono or polysubstituted with at least one of an alkyl group, an alkoxy group or a trihalogenated alkyl group, and wherein the respective ring system of $R^3$ optionally may be attached via a linear or branched, saturated or unsaturated aliphatic $C_{1-5}$ group;
$R^4$ denotes hydrogen, or a phenyl group; and
$R^5$ denotes a linear or branched, saturated or unsaturated aliphatic $C_{1-6}$ group, or a phenyl group optionally substituted with halogen, an alkyl group or an alkoxy group,
or a hydrate thereof or salt thereof with a physiologically acceptable acid.

2. The compound of claim 1, wherein said compound is present in the form of a free base.

3. The compound of claim 1, wherein said compound is present in the form of a pure enantiomer or pure diastereoisomer.

4. The compound of claim 1, wherein said compound is present in the form of a mixture of stereoisomers.

5. The compound of claim 1, wherein said compound is present in the form of a racemic mixture.

6. The compound of claim 1, wherein said compound is present in the form of a hydrate.

7. A compound according to claim 1, wherein
$R^1$ and $R^2$ together form a $(CH_2)_n$ chain, wherein n denotes an integer from 2-9;
$R^3$ denotes a linear or branched, saturated or unsaturated aliphatic $C_{1-3}$ group, a saturated or unsaturated cycloaliphatic $C_{5-6}$ group, a phenyl group or a thienyl group, wherein if $R^3$ is a ring system, the respective ring system of $R^3$ may be unsubstituted or monosubstituted with halogen or mono- or polysubstituted with an alkyl group, an alkoxy group or a trihalogenated alkyl group and optionally may be attached via a linear or branched, saturated or unsaturated aliphatic $C_{1-3}$ group;
$R^4$ denotes hydrogen or a phenyl group; and
$R^5$ denotes a linear or branched, saturated or unsaturated aliphatic $C_{1-3}$ group, or a phenyl group optionally substituted with halogen or an alkoxy group.

8. A compound according to claim 7, wherein the phenyl group of $R^5$ is substituted.

9. A compound according to claim 1, wherein
$R^1$ and $R^2$ together form a $(CH_2)_n$ chain, wherein n denotes 3, 4, 5 or 9;
$R^3$ denotes a vinyl group, a cyclopentyl group, a cyclohexyl group optionally attached via a methylene group, a thienyl group, or a phenyl group optionally monosubstituted with fluorine or chlorine or mono- or polysubstituted with a methyl group, an isopropyl group, a methoxy group or a trifluoroethyl group, and optionally attached via a linear saturated aliphatic $C_{1-3}$ group or an ethynyl group;

$R^4$ denotes hydrogen or a phenyl group; and $R^5$ denotes a methyl group, or a phenyl group optionally substituted with a chlorine atom or a methoxy group.

10. A compound corresponding to formula II

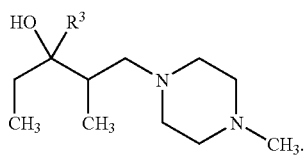

II wherein $R^3$ denotes a linear or branched, saturated or unsaturated aliphatic $C_{1-3}$ group, a saturated or unsaturated cycloaliphatic $C_{5-6}$ group, a phenyl group or a thienyl group, wherein if $R^3$ is a ring system, the respective ring system of $R^3$ may be unsubstituted or monosubstituted with halogen or mono- or polysubstituted with an alkyl group, an alkoxy group or a trihalogenated alkyl group and optionally may be attached via a linear or branched, saturated or unsaturated aliphatic $C_{1-3}$ group.

11. A compound according to claim 1, said compound corresponding to formula IV,

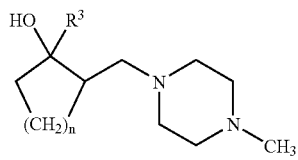

IV wherein n denotes an integer from 2-9.

12. A compound according to claim 1, said compound corresponding to formula V,

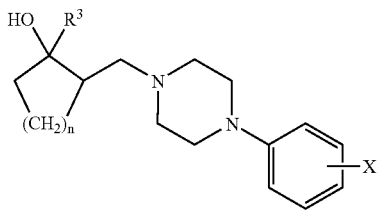

V wherein n denotes an integer from 2-9 and

X denotes hydrogen, halogen or an alkoxy group.

13. A compound according to claim 12, wherein X denotes hydrogen, chlorine or a methoxy group.

14. A compound according to claim 1, said compound corresponding to formula VI,

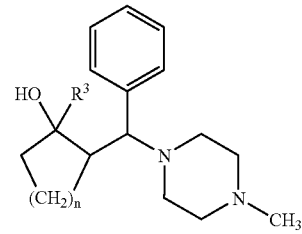

VI wherein n denotes an integer from 2-9.

15. A compound according to claim 1, said compound corresponding to formula VII,

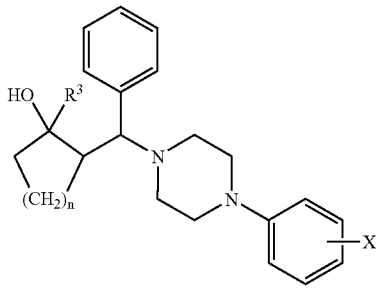

VII wherein n denotes an integer from 2-9 and

X denotes hydrogen, halogen or an alkoxy group.

16. A compound according to claim 15, wherein X denotes hydrogen, chlorine or a methoxy group.

17. A compound according to claim 10, wherein $R^3$ denotes a linear or branched, saturated or unsaturated aliphatic $C_{1-6}$ group, a saturated or unsaturated cycloaliphatic $C_{3-7}$ group, a phenyl group or a thienyl group, wherein the respective ring system may optionally be monosubstituted with halogen or mono- or polysubstituted with at least one of an alkyl group, an alkoxy group and a trihalogenated alkyl group and optionally may be attached via a linear or branched, saturated or unsaturated aliphatic $C_{1-5}$ group.

18. A compound according to claim 11, wherein $R^3$ denotes a linear or branched, saturated or unsaturated aliphatic $C_{1-6}$ group, a saturated or unsaturated cycloaliphatic $C_{3-7}$ group, a phenyl group or a thienyl group, wherein the respective ring system may optionally be monosubstituted with halogen or mono- or polysubstituted with at least one of an alkyl group, an alkoxy group and a trihalogenated alkyl group and optionally may be attached via a linear or branched, saturated or unsaturated aliphatic $C_{1-5}$ group.

19. A compound according to claim 12, wherein $R^3$ denotes a linear or branched, saturated or unsaturated aliphatic $C_{1-6}$ group, a saturated or unsaturated cycloaliphatic $C_{3-7}$ group, a phenyl group or a thienyl group, wherein the respective ring system may optionally be monosubstituted with halogen or mono- or polysubstituted with at least one of an alkyl group, an alkoxy group and a trihalogenated alkyl group and optionally may be attached via a linear or branched, saturated or unsaturated aliphatic $C_{1-5}$ group.

20. A compound according to claim 14, wherein $R^3$ denotes a linear or branched, saturated or unsaturated aliphatic $C_{1-6}$ group, a saturated or unsaturated cycloaliphatic $C_{3-7}$ group, a phenyl group or a thienyl group, wherein the respective ring system may optionally be monosubstituted with halogen or mono- or polysubstituted with at least one of an alkyl group, an alkoxy group and a trihalogenated alkyl group and optionally may be attached via a linear or branched, saturated or unsaturated aliphatic $C_{1-5}$ group.

21. A compound according to claim 15, wherein $R^3$ denotes a linear or branched, saturated or unsaturated aliphatic $C_{1-6}$ group, a saturated or unsaturated cycloaliphatic $C_{3-7}$ group, a phenyl group or a thienyl group, wherein the respective ring system may optionally be monosubstituted with halogen or mono- or polysubstituted with at least one of an alkyl group, an alkoxy group and a trihalogenated alkyl group and optionally may be attached via a linear or branched, saturated or unsaturated aliphatic $C_{1-5}$ group.

22. A compound according to claim 10, wherein $R^3$ denotes a linear or branched, saturated or unsaturated aliphatic $C_{1-3}$ group, a saturated or unsaturated cycloaliphatic $C_{5-6}$ group, a phenyl group or a thienyl group, wherein the respective ring system may optionally be monosubstituted with halogen or mono- or polysubstituted with an alkyl group, an alkoxy group or a trihalogenated alkyl group and optionally may be attached via a linear or branched, saturated or unsaturated aliphatic $C_{1-3}$ group.

23. A compound according to claim 11, wherein $R^3$ denotes a linear or branched, saturated or unsaturated aliphatic $C_{1-3}$ group, a saturated or unsaturated cycloaliphatic $C_{5-6}$ group, a phenyl group or a thienyl group, wherein the respective ring system may optionally be monosubstituted with halogen or mono- or polysubstituted with an alkyl group, an alkoxy group or a trihalogenated alkyl group and optionally may be attached via a linear or branched, saturated or unsaturated aliphatic $C_{1-3}$ group.

24. A compound according to claim 12, wherein $R^3$ denotes a linear or branched, saturated or unsaturated aliphatic $C_{1-3}$ group, a saturated or unsaturated cycloaliphatic $C_{5-6}$ group, a phenyl group or a thienyl group, wherein the respective ring system may optionally be monosubstituted with halogen or mono- or polysubstituted with an alkyl group, an alkoxy group or a trihalogenated alkyl group and optionally may be attached via a linear or branched, saturated or unsaturated aliphatic $C_{1-3}$ group.

25. A compound according to claim 14, wherein $R^3$ denotes a linear or branched, saturated or unsaturated aliphatic $C_{1-3}$ group, a saturated or unsaturated cycloaliphatic $C_{5-6}$ group, a phenyl group or a thienyl group, wherein the respective ring system may optionally be monosubstituted with halogen or mono- or polysubstituted with an alkyl group, an alkoxy group or a trihalogenated alkyl group and optionally may be attached via a linear or branched, saturated or unsaturated aliphatic $C_{1-3}$ group.

26. A compound according to claim 15, wherein $R^3$ denotes a linear or branched, saturated or unsaturated aliphatic $C_{1-3}$ group, a saturated or unsaturated cycloaliphatic $C_{5-6}$ group, a phenyl group or a thienyl group, wherein the respective ring system may optionally be monosubstituted with halogen or mono- or polysubstituted with an alkyl group, an alkoxy group or a trihalogenated alkyl group and optionally may be attached via a linear or branched, saturated or unsaturated aliphatic $C_{1-3}$ group.

27. A compound according to claim 10, wherein $R^3$ denotes a vinyl group, a cyclopentyl group, a cyclohexyl group, a thienyl group or a phenyl group, wherein the cyclohexyl group may optionally be attached via a methylene group or the phenyl group may optionally be monosubstituted with fluorine or chlorine or mono- or polysubstituted with a methyl group, an isopropyl group, a methoxy group or a trifluoroethyl group and may optionally be attached via a linear saturated aliphatic $C_{1-3}$ group or an ethynyl group.

28. A compound according to claim 11, wherein $R^3$ denotes a vinyl group, a cyclopentyl group, a cyclohexyl group, a thienyl group or a phenyl group, wherein the cyclohexyl group may optionally be attached via a methylene group or the phenyl group may optionally be monosubstituted with fluorine or chlorine or mono- or polysubstituted with a methyl group, an isopropyl group, a methoxy group or a trifluoroethyl group and may optionally be attached via a linear saturated aliphatic $C_{1-3}$ a group or an ethynyl group.

29. A compound according to claim 12, wherein $R^3$ denotes a vinyl group, a cyclopentyl group, a cyclohexyl group, a thienyl group or a phenyl group, wherein the cyclohexyl group may optionally be attached via a methylene group or the phenyl group may optionally be monosubstituted with fluorine or chlorine or mono- or polysubstituted with a methyl group, an isopropyl group, a methoxy group or a trifluoroethyl group and may optionally be attached via a linear saturated aliphatic $C_{1-3}$ group or an ethynyl group.

30. A compound according to claim 14, wherein $R^3$ denotes a vinyl group, a cyclopentyl group, a cyclohexyl group, a thienyl group or a phenyl group, wherein the cyclohexyl group may optionally be attached via a methylene group or the phenyl group may optionally be monosubstituted with fluorine or chlorine or mono- or polysubstituted with a methyl group, an isopropyl group, a methoxy group or a trifluoroethyl group and may optionally be attached via a linear saturated aliphatic $C_{1-3}$ group or an ethynyl group.

31. A compound according to claim 15, wherein $R^3$ denotes a vinyl group, a cyclopentyl group, a cyclohexyl group, a thienyl group or a phenyl group, wherein the cyclohexyl group may optionally be attached via a methylene group or the phenyl group may optionally be monosubstituted with fluorine or chlorine or mono- or polysubstituted with a methyl group, an isopropyl group, a methoxy group or a trifluoroethyl group and may optionally be attached via a linear saturated aliphatic $C_{1-3}$ group or an ethynyl group.

32. An N,N'-disubstituted piperazine compound selected from the group consisting of:
    2-Methyl-1-(4-methyl-piperazin-1-yl)-3-phenyl-pentan-3-ol;
    3-(4-Chloro-phenyl)-2-methyl-1-(4-methyl-piperazin-1-yl)-pentan-3-ol;
    3-Benzyl-2-methyl-1-(4-methyl-piperazin-1-yl)-pentan-3-ol;
    3-(4-Fluoro-3-methyl-phenyl)-2-methyl-1-(4-methyl-piperazin-1-yl)-pentan-3-ol;
    2-Methyl-1-(4-methyl-piperazin-1-yl)-3-o-tolyl-pentan-3-ol;
    3-Ethyl-4-methyl-5-(4-methyl-piperazin-1-yl)-pent-1-en-3-ol;
    3-(4-tert-Butyl-phenyl)-2-methyl-1-(4-methyl-piperazin-1-yl)-pentan-3-ol;
    3-Cyclopentyl-2-methyl-1-(4-methyl-piperazin-1-yl)-pentan-3-ol;
    2-Methyl-1-(4-methyl-piperazin-1-yl)-3-m-tolyl-pentan-3-ol;
    3-Cyclohexyl-2-methyl-1-(4-methyl-piperazin-1-yl)-pentan-3-ol;
    3-(4-Fluoro-phenyl)-2-methyl-1-(4-methyl-piperazin-1-yl)-pentan-3-ol;
    3-Ethyl-2-methyl-1-(4-methyl-piperazin-1-yl)-5-phenyl-pentan-3-ol;
    3-Ethyl-4-methyl-5-(4-methyl-piperazin-1-yl)-1-phenyl-pent-1-yn-3-ol;

2-Methyl-1-(4-methyl-piperazin-1-yl)-3-thiophen-2-yl-pentan-3-ol;
3-(3-Methoxy-phenyl)-2-methyl-1-(4-methyl-piperazin-1-yl)-pentan-3-ol;
3-Ethyl-2-methyl-1-(4-methyl-piperazin-1-yl)-6-phenyl-hexan-3-ol;
2-Methyl-1-(4-methyl-piperazin-1-yl)-3-p-tolyl-pentan-3-ol;
3-(4-Methoxy-phenyl)-2-methyl-1-(4-methyl-piperazin-1-yl)-pentan-3-ol;
2-(4-Methyl-piperazin-1-ylmethyl)-1-phenyl-cyclohexanol;
1-Benzyl-2-(4-methyl-piperazin-1-ylmethyl)-cyclohexanol;
1-(4-Fluoro-3-methyl-phenyl)-2-(4-methyl-piperazin-1-ylmethyl)-cyclohexanol;
2-(4-Methyl-piperazin-1-ylmethyl)-1-o-tolyl-cyclohexanol;
2-(4-Methyl-piperazin-1-ylmethyl)-1-vinyl-cyclohexanol;
1-Cyclopentyl-2-(4-methyl-piperazin-1-ylmethyl)-cyclohexanol;
2-(4-Methyl-piperazin-1-ylmethyl)-1-m-tolyl-cyclohexanol;
2-(4-Methyl-piperazin-1-ylmethyl)-bicyclohexyl-1-ol;
1-(4-Fluoro-phenyl)-2-(4-methyl-piperazin-1-ylmethyl)-cyclohexanol;
2-(4-Methyl-piperazin-1-ylmethyl)-1-phenethyl-cyclohexanol;
2-(4-Methyl-piperazin-1-ylmethyl)-1-thiophen-2-yl-cyclohexanol;
1-(2,4-Dichloro-phenyl)-2-(4-methyl-piperazin-1-ylmethyl)-cyclohexanol;
1-(3-Methoxy-phenyl)-2-(4-methyl-piperazin-1-ylmethyl)-cyclohexanol;
2-(4-Methyl-piperazin-1-ylmethyl)-1-(3-phenyl-propyl)-cyclohexanol;
2-(4-Methyl-piperazin-1-ylmethyl)-1-p-tolyl-cyclohexanol;
1-(4-Methoxy-phenyl)-2-(4-methyl-piperazin-1-ylmethyl)-cyclohexanol;
1-Benzyl-2-(4-methyl-piperazin-1-ylmethyl)-cyclooctanol;
2-(4-Methyl-piperazin-1-ylmethyl)-1-vinyl-cyclooctanol;
1-(4-tert-Butyl-phenyl)-2-(4-methyl-piperazin-1-ylmethyl)-cyclooctanol;
1-Cyclopentyl-2-(4-methyl-piperazin-1-ylmethyl)-cyclooctanol;
2-(4-Methyl-piperazin-1-ylmethyl)-1-phenethyl-cyclooctanol;
2-(4-Methyl-piperazin-1-ylmethyl)-1-phenylethynyl-cyclooctanol;
2-(4-Methyl-piperazin-1-ylmethyl)-1-thiophen-2-yl-cyclooctanol;
1-(3-Methoxy-phenyl)-2-(4-methyl-piperazin-1-ylmethyl)-cyclooctanol;
2-(4-Methyl-piperazin-1-ylmethyl)-1-(3-phenyl-propyl)-cyclooctanol;
2-(4-Methyl-piperazin-1-ylmethyl)-1-p-tolyl-cyclooctanol;
1-(4-Methoxy-phenyl)-2-(4-methyl-piperazin-1-ylmethyl)-cyclooctanol;
2-(4-Methyl-piperazin-1-ylmethyl)-1-phenyl-cycloheptanol;
1-(4-Chloro-phenyl)-2-(4-methyl-piperazin-1-ylmethyl)-cycloheptanol;
1-Benzyl-2-(4-methyl-piperazin-1-ylmethyl)-cycloheptanol;
1-(4-Fluoro-3-methyl-phenyl)-2-(4-methyl-piperazin-1-ylmethyl)-cycloheptanol;
2-(4-Methyl-piperazin-1-ylmethyl)-1-o-tolyl-cycloheptanol;
2-(4-Methyl-piperazin-1-ylmethyl)-1-vinyl-cycloheptanol;
1-(4-tert-Butyl-phenyl)-2-(4-methyl-piperazin-1-ylmethyl)-cycloheptanol;
1-Cyclopentyl-2-(4-methyl-piperazin-1-ylmethyl)-cycloheptanol;
2-(4-Methyl-piperazin-1-ylmethyl)-1-m-tolyl-cycloheptanol;
1-[4-(3-Chloro-phenyl)-piperazin-1-yl]-2-methyl-3-phenyl-pentan-3-ol;
3-(4-Chloro-phenyl)-1-[4-(3-chloro-phenyl)-piperazin-1-yl]-2-methyl-pentan-3-ol;
3-Benzyl-1-[4-(3-chloro-phenyl)-piperazin-1-yl]-2-methyl-pentan-3-ol;
1-[4-(3-Chloro-phenyl)-piperazin-1-yl]-3-(4-fluoro-3-methyl-phenyl)-2-methyl-pentan-3-ol;
5-[4-(3-Chloro-phenyl)-piperazin-1-yl]-3-ethyl-4-methyl-pent-1-en-3-ol;
3-(4-tert-Butyl-phenyl)-1-[4-(3-chloro-phenyl)-piperazin-1-yl]-2-methyl-pentan-3-ol;
1-[4-(3-Chloro-phenyl)-piperazin-1-yl]-2-methyl-3-m-tolyl-pentan-3-ol;
1-[4-(3-Chloro-phenyl)-piperazin-1-yl]-3-cyclohexyl-2-methyl-pentan-3-ol;
1-[4-(3-Chloro-phenyl)-piperazin-1-yl]-3-(4-fluoro-phenyl)-2-methyl-pentan-3-ol;
1-[4-(3-Chloro-phenyl)-piperazin-1-yl]-3-ethyl-2-methyl-5-phenyl-pentan-3-ol;
5-[4-(3-Chloro-phenyl)-piperazin-1-yl]-3-ethyl-4-methyl-1-phenyl-pent-1-yn-3-ol;
1-[4-(3-Chloro-phenyl)-piperazin-1-yl]-2-methyl-3-thiophen-2-yl-pentan-3-ol;
1-[4-(3-Chloro-phenyl)-piperazin-1-yl]-3-(3-methoxy-phenyl)-2-methyl-pentan-3-ol;
1-[4-(3-Chloro-phenyl)-piperazin-1-yl]-3-ethyl-2-methyl-6-phenyl-hexan-3-ol;
1-[4-(3-Chloro-phenyl)-piperazin-1-yl]-2-methyl-3-p-tolyl-pentan-3-ol;
1-[4-(3-Chloro-phenyl)-piperazin-1-yl]-3-(4-methoxy-phenyl)-2-methyl-pentan-3-ol;
1-[4-(3-Chloro-phenyl)-piperazin-1-yl]-3-(5-fluoro-2-methoxy-phenyl)-2-methyl-pentan-3-ol;
1-[4-(3-Chloro-phenyl)-piperazin-1-yl]-3-(3-fluoro-phenyl)-2-methyl-pentan-3-ol;
3-(3-Chloro-phenyl)-1-[4-(3-chloro-phenyl)-piperazin-1-yl]-2-methyl-pentan-3-ol;
3-(2-Chloro-benzyl)-1-[4-(3-chloro-phenyl)-piperazin-1-yl]-2-methyl-pentan-3-ol;
1-[4-(3-Chloro-phenyl)-piperazin-1-yl]-3-(4-fluoro-benzyl)-2-methyl-pentan-3-ol;
1-[4-(3-Chloro-phenyl)-piperazin-1-yl]-3-(3-methoxy-benzyl)-2-methyl-pentan-3-ol;
1-[4-(3-Chloro-phenyl)-piperazin-1-yl]-3-(3-fluoro-benzyl)-2-methyl-pentan-3-ol;
1-[4-(3-Chloro-phenyl)-piperazin-1-yl]-3-(2-methoxy-phenyl)-2-methyl-pentan-3-ol;
1-[4-(3-Chloro-phenyl)-piperazin-1-yl]-2-methyl-3-(2-methyl-benzyl)-pentan-3-ol;
1-[4-(3-Chloro-phenyl)-piperazin-1-yl]-2-methyl-3-(3-trifluoromethyl-phenyl)-pentan-3-ol;

1-[4-(3-Chloro-phenyl)-piperazin-1-yl]-2-methyl-3-(3-methyl-benzyl)-pentan-3-ol;
3-(4-Chloro-benzyl)-1-[4-(3-chloro-phenyl)-piperazin-1-yl]-2-methyl-pentan-3-ol;
3-(2-Chloro-6-fluoro-benzyl)-1-[4-(3-chloro-phenyl)-piperazin-1-yl]-2-methyl-pentan-3-ol;
1-[4-(3-Chloro-phenyl)-piperazin-1-yl]-3-(2,5-dimethyl-benzyl)-2-methyl-pentan-3-ol;
3-(3-Chloro-benzyl)-1-[4-(3-chloro-phenyl)-piperazin-1-yl]-2-methyl-pentan-3-ol;
1-[4-(3-Chloro-phenyl)-piperazin-1-yl]-3-(2,4-dichloro-benzyl)-2-methyl-pentan-3-ol;
3-Cyclohexylmethyl-2-methyl-1-(4-methyl-piperazin-1-yl)-pentan-3-ol;
3-(5-Fluoro-2-methoxy-phenyl)-2-methyl-1-(4-methyl-piperazin-1-yl)-pentan-3-ol;
3-(3-Fluoro-phenyl)-2-methyl-1-(4-methyl-piperazin-1-yl)-pentan-3-ol;
3-(3-Chloro-phenyl)-2-methyl-1-(4-methyl-piperazin-1-yl)-pentan-3-ol;
3-(3,5-Dichloro-phenyl)-2-methyl-1-(4-methyl-piperazin-1-yl)-pentan-3-ol;
3-(2-Chloro-benzyl)-2-methyl-1-(4-methyl-piperazin-1-yl)-pentan-3-ol;
3-(4-Fluoro-benzyl)-2-methyl-1-(4-methyl-piperazin-1-yl)-pentan-3-ol;
3-(3-Methoxy-benzyl)-2-methyl-1-(4-methyl-piperazin-1-yl)-pentan-3-ol;
3-(4-Chloro-3-trifluoromethyl-phenyl)-2-methyl-1-(4-methyl-piperazin-1-yl)-pentan-3-ol;
3-(3-Fluoro-benzyl)-2-methyl-1-(4-methyl-piperazin-1-yl)-pentan-3-ol;
3-(2-Methoxy-phenyl)-2-methyl-1-(4-methyl-piperazin-1-yl)-pentan-3-ol;
2-Methyl-3-(2-methyl-benzyl)-1-(4-methyl-piperazin-1-yl)-pentan-3-ol;
3-(3-Chloro-4-fluoro-phenyl)-2-methyl-1-(4-methyl-piperazin-1-yl)-pentan-3-ol;
2-Methyl-1-(4-methyl-piperazin-1-yl)-3-(3-trifluoromethyl-phenyl)-pentan-3-ol;
2-Methyl-3-(3-methyl-benzyl)-1-(4-methyl-piperazin-1-yl)-pentan-3-ol;
3-(4-Chloro-benzyl)-2-methyl-1-(4-methyl-piperazin-1-yl)-pentan-3-ol;
3-(2-Chloro-6-fluoro-benzyl)-2-methyl-1-(4-methyl-piperazin-1-yl)-pentan-3-ol;
3-(2,5-Dimethyl-benzyl)-2-methyl-1-(4-methyl-piperazin-1-yl)-pentan-3-ol;
3-(3-Chloro-benzyl)-2-methyl-1-(4-methyl-piperazin-1-yl)-pentan-3-ol;
3-(2,4-Dichloro-benzyl)-2-methyl-1-(4-methyl-piperazin-1-yl)-pentan-3-ol;
1-Cyclohexylmethyl-2-(4-methyl-piperazin-1-ylmethyl)-cyclohexanol;
1-(5-Fluoro-2-methoxy-phenyl)-2-(4-methyl-piperazin-1-ylmethyl)-cyclohexanol;
1-(3-Fluoro-phenyl)-2-(4-methyl-piperazin-1-ylmethyl)-cyclohexanol;
1-(3-Chloro-phenyl)-2-(4-methyl-piperazin-1-ylmethyl)-cyclohexanol;
1-(3,5-Dichloro-phenyl)-2-(4-methyl-piperazin-1-ylmethyl)-cyclohexanol;
1-(2-Chloro-benzyl)-2-(4-methyl-piperazin-1-ylmethyl)-cyclohexanol;
1-(4-Fluoro-benzyl)-2-(4-methyl-piperazin-1-ylmethyl)-cyclohexanol;
1-(3-Methoxy-benzyl)-2-(4-methyl-piperazin-1-ylmethyl)-cyclohexanol;
1-(4-Chloro-3-trifluoromethyl-phenyl)-2-(4-methyl-piperazin-1-ylmethyl)-cyclohexanol;
1-(3-Fluoro-benzyl)-2-(4-methyl-piperazin-1-ylmethyl)-cyclohexanol;
1-(2-Methoxy-phenyl)-2-(4-methyl-piperazin-1-ylmethyl)-cyclohexanol;
1-(2-Methyl-benzyl)-2-(4-methyl-piperazin-1-ylmethyl)-cyclohexanol;
1-(3-Chloro-4-fluoro-phenyl)-2-(4-methyl-piperazin-1-ylmethyl)-cyclohexanol;
2-(4-Methyl-piperazin-1-ylmethyl)-1-(3-trifluoromethyl-phenyl)-cyclohexanol;
1-(3-Methyl-benzyl)-2-(4-methyl-piperazin-1-ylmethyl)-cyclohexanol;
1-(4-Chloro-benzyl)-2-(4-methyl-piperazin-1-ylmethyl)-cyclohexanol;
1-(2,5-Dimethyl-benzyl)-2-(4-methyl-piperazin-1-ylmethyl)-cyclohexanol;
1-(3-Chloro-benzyl)-2-(4-methyl-piperazin-1-ylmethyl)-cyclohexanol;
1-(2,4-Dichloro-benzyl)-2-(4-methyl-piperazin-1-ylmethyl)-cyclohexanol;
1-Cyclohexylmethyl-2-(4-methyl-piperazin-1-ylmethyl)-cyclooctanol;
1-(5-Fluoro-2-methoxy-phenyl)-2-(4-methyl-piperazin-1-ylmethyl)-cyclooctanol;
1-(2-Chloro-benzyl)-2-(4-methyl-piperazin-1-ylmethyl)-cyclooctanol;
1-(4-Fluoro-benzyl)-2-(4-methyl-piperazin-1-ylmethyl)-cyclooctanol;
1-(3-Fluoro-benzyl)-2-(4-methyl-piperazin-1-ylmethyl)-cyclooctanol;
1-(2-Methoxy-phenyl)-2-(4-methyl-piperazin-1-ylmethyl)-cyclooctanol;
1-(3-Methyl-benzyl)-2-(4-methyl-piperazin-1-ylmethyl)-cyclooctanol;
1-(4-Chloro-benzyl)-2-(4-methyl-piperazin-1-ylmethyl)-cyclooctanol;
1-(2-Chloro-6-fluoro-benzyl)-2-(4-methyl-piperazin-1-ylmethyl)-cyclooctanol;
1-(2,5-Dimethyl-benzyl)-2-(4-methyl-piperazin-1-ylmethyl)-cyclooctanol;
1-(3-Chloro-benzyl)-2-(4-methyl-piperazin-1-ylmethyl)-cyclooctanol;
1-(2,4-Dichloro-benzyl)-2-(4-methyl-piperazin-1-ylmethyl)-cyclooctanol;
1-Cyclohexylmethyl-2-(4-methyl-piperazin-1-ylmethyl)-cycloheptanol;
1-(5-Fluoro-2-methoxy-phenyl)-2-(4-methyl-piperazin-1-ylmethyl)-cycloheptanol;
1-(3-Fluoro-phenyl)-2-(4-methyl-piperazin-1-ylmethyl)-cycloheptanol;
1-(3-Chloro-phenyl)-2-(4-methyl-piperazin-1-ylmethyl)-cycloheptanol;
1-(3,5-Dichloro-phenyl)-2-(4-methyl-piperazin-1-ylmethyl)-cycloheptanol;
1-(2-Chloro-benzyl)-2-(4-methyl-piperazin-1-ylmethyl)-cycloheptanol;
1-(4-Fluoro-benzyl)-2-(4-methyl-piperazin-1-ylmethyl)-cycloheptanol;
1-(3-Methoxy-benzyl)-2-(4-methyl-piperazin-1-ylmethyl)-cycloheptanol;
1-(4-Chloro-3-trifluoromethyl-phenyl)-2-(4-methyl-piperazin-1-ylmethyl)-cycloheptanol;

1-(3-Fluoro-benzyl)-2-(4-methyl-piperazin-1-ylmethyl)-cycloheptanol;
1-(2-Methoxy-phenyl)-2-(4-methyl-piperazin-1-ylmethyl)-cycloheptanol;
1-(2-Methyl-benzyl)-2-(4-methyl-piperazin-1-ylmethyl)-cycloheptanol;
1-(3-Chloro-4-fluoro-phenyl)-2-(4-methyl-piperazin-1-ylmethyl)-cycloheptanol;
2-(4-Methyl-piperazin-1-ylmethyl)-1-(3-trifluoromethyl-phenyl)-cycloheptanol;
1-(3-Methyl-benzyl)-2-(4-methyl-piperazin-1-ylmethyl)-cycloheptanol;
1-(4-Chloro-benzyl)-2-(4-methyl-piperazin-1-ylmethyl)-cycloheptanol;
1-(2-Chloro-6-fluoro-benzyl)-2-(4-methyl-piperazin-1-ylmethyl)-cycloheptanol;
1-(2,5-Dimethyl-benzyl)-2-(4-methyl-piperazin-1-ylmethyl)-cycloheptanol;
1-(3-Chloro-benzyl)-2-(4-methyl-piperazin-1-ylmethyl)-cycloheptanol;
1-(2,4-Dichloro-benzyl)-2-(4-methyl-piperazin-1-ylmethyl)-cycloheptanol;
1-Benzyl-2-(4-methyl-piperazin-1-ylmethyl)-cyclododecanol;
2-(4-Methyl-piperazin-1-ylmethyl)-1-vinyl-cyclododecanol;
1-Cyclopentyl-2-(4-methyl-piperazin-1-ylmethyl)-cyclododecanol;
2-(4-Methyl-piperazin-1-ylmethyl)-1-phenethyl-cyclododecanol;
2-(4-Methyl-piperazin-1-ylmethyl)-1-phenylethynyl-cyclododecanol;
2-(4-Methyl-piperazin-1-ylmethyl)-1-thiophen-2-yl-cyclododecanol;
2-(4-Methyl-piperazin-1-ylmethyl)-1-(3-phenyl-propyl)-cyclododecanol;
1-(5-Fluoro-2-methoxy-phenyl)-2-(4-methyl-piperazin-1-ylmethyl)-cyclododecanol;
1-(2-Chloro-benzyl)-2-(4-methyl-piperazin-1-ylmethyl)-cyclododecanol;
1-(4-Fluoro-benzyl)-2-(4-methyl-piperazin-1-ylmethyl)-cyclododecanol;
1-(3-Methoxy-benzyl)-2-(4-methyl-piperazin-1-ylmethyl)-cyclododecanol;
1-(3-Fluoro-benzyl)-2-(4-methyl-piperazin-1-ylmethyl)-cyclododecanol;
1-(2-Methoxy-phenyl)-2-(4-methyl-piperazin-1-ylmethyl)-cyclododecanol;
1-(2-Methyl-benzyl)-2-(4-methyl-piperazin-1-ylmethyl)-cyclododecanol;
1-(3-Methyl-benzyl)-2-(4-methyl-piperazin-1-ylmethyl)-cyclododecanol;
1-(4-Chloro-benzyl)-2-(4-methyl-piperazin-1-ylmethyl)-cyclododecanol;
1-(2,5-Dimethyl-benzyl)-2-(4-methyl-piperazin-1-ylmethyl)-cyclododecanol;
1-(3-Chloro-benzyl)-2-(4-methyl-piperazin-1-ylmethyl)-cyclododecanol;
1-(2,4-Dichloro-benzyl)-2-(4-methyl-piperazin-1-ylmethyl)-cyclododecanol;
2-[4-(3-Chloro-phenyl)-piperazin-1-ylmethyl]-1-cyclohexylmethyl-cyclohexanol;
2-[4-(3-Chloro-phenyl)-piperazin-1-ylmethyl]-1-(5-fluoro-2-methoxy-phenyl)-cyclohexanol;
2-[4-(3-Chloro-phenyl)-piperazin-1-ylmethyl]-1-(3-fluoro-phenyl)-cyclohexanol;
1-(3-Chloro-phenyl)-2-[4-(3-chloro-phenyl)-piperazin-1-ylmethyl]-cyclohexanol;
2-[4-(3-Chloro-phenyl)-piperazin-1-ylmethyl]-1-(3,5-dichloro-phenyl)-cyclohexanol;
1-(2-Chloro-benzyl)-2-[4-(3-chloro-phenyl)-piperazin-1-ylmethyl]-cyclohexanol;
2-[4-(3-Chloro-phenyl)-piperazin-1-ylmethyl]-1-(4-fluoro-benzyl)-cyclohexanol;
2-[4-(3-Chloro-phenyl)-piperazin-1-ylmethyl]-1-(4-chloro-3-trifluoromethyl-phenyl)-cyclohexanol;
2-[4-(3-Chloro-phenyl)-piperazin-1-ylmethyl]-1-(3-fluoro-benzyl)-cyclohexanol;
2-[4-(3-Chloro-phenyl)-piperazin-1-ylmethyl]-1-(2-methoxy-phenyl)-cyclohexanol;
1-(3-Chloro-4-fluoro-phenyl)-2-[4-(3-chloro-phenyl)-piperazin-1-ylmethyl]-cyclohexanol;
2-[4-(3-Chloro-phenyl)-piperazin-1-ylmethyl]-1-(3-trifluoromethyl-phenyl)-cyclohexanol;
2-[4-(3-Chloro-phenyl)-piperazin-1-ylmethyl]-1-(3-methyl-benzyl)-cyclohexanol;
1-(4-Chloro-benzyl)-2-[4-(3-chloro-phenyl)-piperazin-1-ylmethyl]-cyclohexanol;
1-(2-Chloro-6-fluoro-benzyl)-2-[4-(3-chloro-phenyl)-piperazin-1-ylmethyl]-cyclohexanol;
2-[4-(3-Chloro-phenyl)-piperazin-1-ylmethyl]-1-(2,5-dimethyl-benzyl)-cyclohexanol;
1-(3-Chloro-benzyl)-2-[4-(3-chloro-phenyl)-piperazin-1-ylmethyl]-cyclohexanol;
2-[4-(2-Chloro-phenyl)-piperazin-1-ylmethyl]-1-phenyl-cyclohexanol;
1-(4-Chloro-phenyl)-2-[4-(2-chloro-phenyl)-piperazin-1-ylmethyl]-cyclohexanol;
1-Benzyl-2-[4-(2-chloro-phenyl)-piperazin-1-ylmethyl]-cyclohexanol;
2-[4-(2-Chloro-phenyl)-piperazin-1-ylmethyl]-1-(4-fluoro-3-methyl-phenyl)-cyclohexanol;
2-[4-(2-Chloro-phenyl)-piperazin-1-ylmethyl]-1-o-tolyl-cyclohexanol;
2-[4-(2-Chloro-phenyl)-piperazin-1-ylmethyl]-1-vinyl-cyclohexanol;
1-(4-tert-Butyl-phenyl)-2-[4-(2-chloro-phenyl)-piperazin-1-ylmethyl]-cyclohexanol;
2-[4-(2-Chloro-phenyl)-piperazin-1-ylmethyl]-1-cyclopentyl-cyclohexanol;
2-[4-(2-Chloro-phenyl)-piperazin-1-ylmethyl]-1-m-tolyl-cyclohexanol;
2-[4-(2-Chloro-phenyl)-piperazin-1-ylmethyl]-bicyclohexyl-1-ol;
2-[4-(2-Chloro-phenyl)-piperazin-1-ylmethyl]-1-(4-fluoro-phenyl)-cyclohexanol;
2-[4-(2-Chloro-phenyl)-piperazin-1-ylmethyl]-1-phenethyl-cyclohexanol;
2-[4-(2-Chloro-phenyl)-piperazin-1-ylmethyl]-1-phenylethynyl-cyclohexanol;
2-[4-(2-Chloro-phenyl)-piperazin-1-ylmethyl]-1-thiophen-2-yl-cyclohexanol;
2-[4-(2-Chloro-phenyl)-piperazin-1-ylmethyl]-1-(3-methoxy-phenyl)-cyclohexanol;
2-[4-(2-Chloro-phenyl)-piperazin-1-ylmethyl]-1-(3-phenyl-propyl)-cyclohexanol;
2-[4-(2-Chloro-phenyl)-piperazin-1-ylmethyl]-1-p-tolyl-cyclohexanol;
2-[4-(2-Chloro-phenyl)-piperazin-1-ylmethyl]-1-(4-methoxy-phenyl)-cyclohexanol;
2-[4-(2-Chloro-phenyl)-piperazin-1-ylmethyl]-1-cyclohexylmethyl-cyclohexanol;

2-[4-(2-Chloro-phenyl)-piperazin-1-ylmethyl]-1-(5-fluoro-2-methoxy-phenyl)-cyclohexanol;
1-(3-Chloro-phenyl)-2-[4-(2-chloro-phenyl)-piperazin-1-ylmethyl]-cyclohexanol;
2-[4-(2-Chloro-phenyl)-piperazin-1-ylmethyl]-1-(3,5-dichloro-phenyl)-cyclohexanol;
1-(2-Chloro-benzyl)-2-[4-(2-chloro-phenyl)-piperazin-1-ylmethyl]-cyclohexanol;
2-[4-(2-Chloro-phenyl)-piperazin-1-ylmethyl]-1-(4-fluoro-benzyl)-cyclohexanol;
2-[4-(2-Chloro-phenyl)-piperazin-1-ylmethyl]-1-(3-methoxy-benzyl)-cyclohexanol;
2-[4-(2-Chloro-phenyl)-piperazin-1-ylmethyl]-1-(4-chloro-3-trifluoromethyl-phenyl)-cyclohexanol;
2-[4-(2-Chloro-phenyl)-piperazin-1-ylmethyl]-1-(3-fluoro-benzyl)-cyclohexanol;
2-[4-(2-Chloro-phenyl)-piperazin-1-ylmethyl]-1-(2-methoxy-phenyl)-cyclohexanol;
2-[4-(2-Chloro-phenyl)-piperazin-1-ylmethyl]-1-(2-methyl-benzyl)-cyclohexanol;
1-(3-Chloro-4-fluoro-phenyl)-2-[4-(2-chloro-phenyl)-piperazin-1-ylmethyl]-cyclohexanol;
2-[4-(2-Chloro-phenyl)-piperazin-1-ylmethyl]-1-(3-trifluoromethyl-phenyl)-cyclohexanol;
2-[4-(2-Chloro-phenyl)-piperazin-1-ylmethyl]-1-(3-methyl-benzyl)-cyclohexanol;
1-(4-Chloro-benzyl)-2-[4-(2-chloro-phenyl)-piperazin-1-ylmethyl]-cyclohexanol;
1-(2-Chloro-6-fluoro-benzyl)-2-[4-(2-chloro-phenyl)-piperazin-1-ylmethyl]-cyclohexanol;
2-[4-(2-Chloro-phenyl)-piperazin-1-ylmethyl]-1-(2,5-dimethyl-benzyl)-cyclohexanol;
1-(3-Chloro-benzyl)-2-[4-(2-chloro-phenyl)-piperazin-1-ylmethyl]-cyclohexanol;
2-[4-(2-Chloro-phenyl)-piperazin-1-ylmethyl]-1-(2,4-dichloro-benzyl)-cyclohexanol;
2-[4-(2-Methoxy-phenyl)-piperazin-1-ylmethyl]-1-phenyl-cyclohexanol;
1-(4-Chloro-phenyl)-2-[4-(2-methoxy-phenyl)-piperazin-1-ylmethyl]-cyclohexanol;
1-Benzyl-2-[4-(2-methoxy-phenyl)-piperazin-1-ylmethyl]-cyclohexanol;
1-(4-Fluoro-3-methyl-phenyl)-2-[4-(2-methoxy-phenyl)-piperazin-1-ylmethyl]-cyclohexanol;
2-[4-(2-Methoxy-phenyl)-piperazin-1-ylmethyl]-1-o-tolyl-cyclohexanol;
2-[4-(2-Methoxy-phenyl)-piperazin-1-ylmethyl]-1-vinyl-cyclohexanol;
1-(4-tert-Butyl-phenyl)-2-[4-(2-methoxy-phenyl)-piperazin-1-ylmethyl]-cyclohexanol;
1-Cyclopentyl-2-[4-(2-methoxy-phenyl)-piperazin-1-ylmethyl]-cyclohexanol;
2-[4-(2-Methoxy-phenyl)-piperazin-1-ylmethyl]-1-m-tolyl-cyclohexanol;
2-[4-(2-Methoxy-phenyl)-piperazin-1-ylmethyl]-bicyclohexyl-1-ol;
1-(4-Fluoro-phenyl)-2-[4-(2-methoxy-phenyl)-piperazin-1-ylmethyl]-cyclohexanol;
2-[4-(2-Methoxy-phenyl)-piperazin-1-ylmethyl]-1-phenethyl-cyclohexanol;
2-[4-(2-Methoxy-phenyl)-piperazin-1-ylmethyl]-1-phenylethynyl-cyclohexanol;
2-[4-(2-Methoxy-phenyl)-piperazin-1-ylmethyl]-1-thiophen-2-yl-cyclohexanol;
1-(3-Methoxy-phenyl)-2-[4-(2-methoxy-phenyl)-piperazin-1-ylmethyl]-cyclohexanol;
2-[4-(2-Methoxy-phenyl)-piperazin-1-ylmethyl]-1-(3-phenyl-propyl)-cyclohexanol;
1-(2,3-Dichloro-phenyl)-2-[4-(2-methoxy-phenyl)-piperazin-1-ylmethyl]-cyclohexanol;
2-[4-(2-Methoxy-phenyl)-piperazin-1-ylmethyl]-1-p-tolyl-cyclohexanol;
1-(4-Methoxy-phenyl)-2-[4-(2-methoxy-phenyl)-piperazin-1-ylmethyl]-cyclohexanol;
1-Cyclohexylmethyl-2-[4-(2-methoxy-phenyl)-piperazin-1-ylmethyl]-cyclohexanol;
1-(5-Fluoro-2-methoxy-phenyl)-2-[4-(2-methoxy-phenyl)-piperazin-1-ylmethyl]-cyclohexanol;
1-(3-Fluoro-phenyl)-2-[4-(2-methoxy-phenyl)-piperazin-1-ylmethyl]-cyclohexanol;
1-(3-Chloro-phenyl)-2-[4-(2-methoxy-phenyl)-piperazin-1-ylmethyl]-cyclohexanol;
1-(3,5-Dichloro-phenyl)-2-[4-(2-methoxy-phenyl)-piperazin-1-ylmethyl]-cyclohexanol;
1-(2-Chloro-benzyl)-2-[4-(2-methoxy-phenyl)-piperazin-1-ylmethyl]-cyclohexanol;
1-(4-Fluoro-benzyl)-2-[4-(2-methoxy-phenyl)-piperazin-1-ylmethyl]-cyclohexanol;
1-(3-Methoxy-benzyl)-2-[4-(2-methoxy-phenyl)-piperazin-1-ylmethyl]-cyclohexanol;
1-(4-Chloro-3-trifluoromethyl-phenyl)-2-[4-(2-methoxy-phenyl)-piperazin-1-ylmethyl]-cyclohexanol;
1-(3-Fluoro-benzyl)-2-[4-(2-methoxy-phenyl)-piperazin-1-ylmethyl]-cyclohexanol;
1-(2-Methoxy-phenyl)-2-[4-(2-methoxy-phenyl)-piperazin-1-ylmethyl]-cyclohexanol;
2-[4-(2-Methoxy-phenyl)-piperazin-1-ylmethyl]-1-(2-methyl-benzyl)-cyclohexanol;
1-(3-Chloro-4-fluoro-phenyl)-2-[4-(2-methoxy-phenyl)-piperazin-1-ylmethyl]-cyclohexanol;
2-[4-(2-Methoxy-phenyl)-piperazin-1-ylmethyl]-1-(3-trifluoromethyl-phenyl)-cyclohexanol;
2-[4-(2-Methoxy-phenyl)-piperazin-1-ylmethyl]-1-(3-methyl-benzyl)-cyclohexanol;
1-(4-Chloro-benzyl)-2-[4-(2-methoxy-phenyl)-piperazin-1-ylmethyl]-cyclohexanol;
1-(2-Chloro-6-fluoro-benzyl)-2-[4-(2-methoxy-phenyl)-piperazin-1-ylmethyl]-cyclohexanol;
1-(2,5-Dimethyl-benzyl)-2-[4-(2-methoxy-phenyl)-piperazin-1-ylmethyl]-cyclohexanol;
1-(3-Chloro-benzyl)-2-[4-(2-methoxy-phenyl)-piperazin-1-ylmethyl]-cyclohexanol;
1-(2,4-Dichloro-benzyl)-2-[4-(2-methoxy-phenyl)-piperazin-1-ylmethyl]-cyclohexanol;
1-Benzyl-2-[4-(2-methoxy-phenyl)-piperazin-1-ylmethyl]-cyclododecanol;
2-[4-(2-Methoxy-phenyl)-piperazin-1-ylmethyl]-1-vinyl-cyclododecanol;
1-Phenethyl-2-[phenyl-(4-phenyl-piperazin-1-yl)-methyl]-cyclohexanol;
1-Benzyl-2-[(4-methyl-piperazin-1-yl)-phenyl-methyl]-cyclohexanol;
1-Benzyl-2-[phenyl-(4-phenyl-piperazin-1-yl)-methyl]-cyclohexanol;
2-[(4-Methyl-piperazin-1-yl)-phenyl-methyl]-1-phenethyl-cyclohexanol; and
2-[4-(2-Methoxy-phenyl)-piperazin-1-ylmethyl]-1-phenethyl-cyclododecanol.

33. A method for producing an N,N'-disubstituted piperazine compound according to claim 32, comprising the steps of:
$A_1$) reacting a ketone corresponding to formula (1),

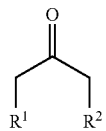

(1)

with paraformaldehyde and a piperazine corresponding to formula (2),

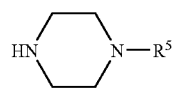

(2)

by a Mannich reaction in a suitable solvent; working up the reaction mixture; and isolating the product corresponding to formula (3)

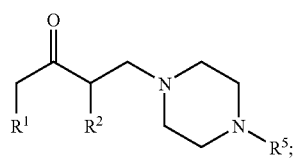

(3)

$A_2$) reacting an enamine corresponding to formula (1a), wherein R denotes an aliphatic $C_{1-6}$ residue, a morpholinyl, piperidyl or pyrrolidinyl residue, wherein the two residues R are the same or different,

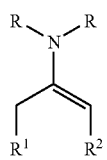

(1a)

with an aldehyde corresponding to formula (4), wherein $R^4$ is not hydrogen

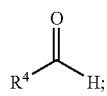

(4)

and a piperazine corresponding to formula (2),

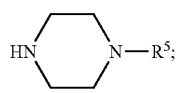

(2)

by a Mannich reaction in the presence of triethylamine, chlorotrimethylsilane and sodium iodide in a suitable solvent;
working up the reaction mixture; and
isolating the product corresponding to formula (3a)

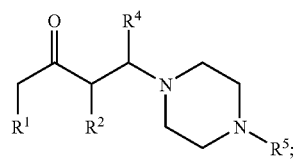

(3a)

$A_3$) reacting an enamine corresponding to formula (1a), wherein R denotes an aliphatic $C_{1-6}$ residue, a morpholinyl, piperidyl or pyrrolidinyl residue, wherein the two residues R are the same or different

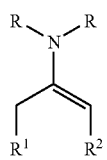

(1a)

with an iminium salt corresponding to formula (5), wherein $R^4$ is not hydrogen and Y— denotes a chloride, bromide, iodide or $AlCl_4$— ion,

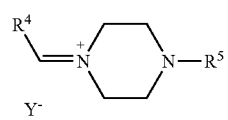

(5)

by a Mannich reaction in a suitable solvent; working up the reaction mixture; and
isolating the product corresponding to formula (3a)

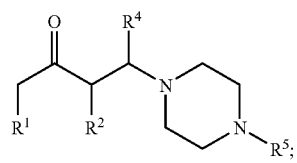

(3a)

B) reacting a compound corresponding to formula (3) or (3a) with a Grignard compound or an organolithium compound corresponding to formulae $R^3MgCl$, $R^3MgBr$, $R^3MgI$, $MgR^3_2$ or $LiR^3$, in a suitable solvent;
working up the reaction mixture; and
isolating the resulting compound.

34. The method of claim 33, wherein in step $A_2$), the piperazine corresponding to formula (2) is provided in the form of the hydrochloride thereof.

35. The method of claim 33, wherein the solvent of step $A_2$) or $A_3$) is acetonitrile.

36. The method of claim 33, wherein the solvent of step B) is diethyl ether or tetrahydrofuran.

37. A pharmaceutical formulation comprising at least one compound according to claim 1 as active ingredient and a physiologically acceptable auxiliary substance.

38. A pharmaceutical formulation comprising a compound according to claim 32, and at least one physiologically acceptable auxiliary substance.

39. A method of alleviating pain in a larger mammal comprising the step of administering to said mammal an effective pain-alleviating amount of a pharmaceutical formulation according to claim 38.

40. A method of anaesthetizing a mammal comprising the step of administering to said mammal an anaesthetically effective amount of a pharmaceutical formulation according to claim 38.

41. A method of treating a disease or condition selected from the group consisting of arrhythmia, urinary incontinence, inflammation and depression, in a mammal comprising the step of administering to said mammal an effective amount of a compound according to claim 32.

42. The method of claim 33, wherein the solvent of step $A_1$) is ethanol with the addition of hydrochloric acid or is acetic acid, or with heating provided to said Mannich reaction.

43. The compound of claim 1, wherein $R^4$ is phenyl.

44. A pharmaceutical formulation comprising a compound according to claim 10, and at least one physiologically acceptable auxiliary substance.

* * * * *